(12) United States Patent
Golub et al.

(10) Patent No.: US 11,045,390 B2
(45) Date of Patent: Jun. 29, 2021

(54) SYSTEMS AND METHODS FOR DELIVERY OF A THERAPEUTIC AGENT

(71) Applicants: TearClear Corp., Copley, OH (US); University of Florida Research Foundation, Incorporated, Gainesville, FL (US)

(72) Inventors: Howard L. Golub, Copley, OH (US); Anuj Chauhan, Golden, CO (US); Michael Williams, Copely, OH (US)

(73) Assignees: TEARCLEAR CORP., Copley, OH (US); UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 16/376,387

(22) Filed: Apr. 5, 2019

(65) Prior Publication Data
US 2019/0307641 A1   Oct. 10, 2019

Related U.S. Application Data

(60) Provisional application No. 62/827,743, filed on Apr. 1, 2019, provisional application No. 62/654,089, filed on Apr. 6, 2018.

(51) Int. Cl.
*A61F 9/00* (2006.01)
*A61J 1/14* (2006.01)
(Continued)

(52) U.S. Cl.
CPC ............ *A61J 1/1456* (2015.05); *A61F 9/0008* (2013.01); *B05B 1/14* (2013.01); *B05B 1/34* (2013.01);
(Continued)

(58) Field of Classification Search
CPC ...... A61J 1/1468; A61J 1/1475; A61J 1/1456; B01D 39/1676; A61F 9/0008;
(Continued)

(56) References Cited

U.S. PATENT DOCUMENTS 4,925,017 A   5/1990   Jessen
4,934,402 A   6/1990   Tarnay et al.
(Continued)

FOREIGN PATENT DOCUMENTS

GB       2021429 B       8/1982
WO    WO-2018102817 A1   6/2018
WO    WO-2019060846 A1   3/2019

OTHER PUBLICATIONS

Baudouin, et al. Short term comparative study of topical 2% carteolol with and without benzalkonium chloride in healthy volunteers. Br J Ophthalmol. Jan. 1998; 82(1): 39-42.
(Continued)

*Primary Examiner* — Kai H Weng
(74) *Attorney, Agent, or Firm* — Wilson Sonsini Goodrich & Rosati

(57) ABSTRACT

The present disclosure relates to nozzles for removing a preservative from a fluid comprising a therapeutic agent to an eye. More particularly, the nozzles disclosed herein may minimize patient exposure to preservative by rapidly and selectively removing a preservative from a solution comprising a therapeutic agent. An example nozzle may comprise a flow diverter which directs a flow path from a fluid inlet to a fluid outlet over a length longer than the distance from the inlet to the outlet. In some cases, the nozzle may comprise a preservative removing agent.

19 Claims, 14 Drawing Sheets

(51) Int. Cl.
  *B65D 47/06* (2006.01)
  *B65D 25/42* (2006.01)
  *B05B 1/34* (2006.01)
  *B65D 41/20* (2006.01)
  *B65D 35/28* (2006.01)
  *B05B 1/14* (2006.01)

(52) U.S. Cl.
  CPC ............. *B65D 25/42* (2013.01); *B65D 35/28* (2013.01); *B65D 41/20* (2013.01); *B65D 47/06* (2013.01); *B65D 2547/06* (2013.01); *B65D 2555/00* (2013.01)

(58) Field of Classification Search
  CPC .. B05B 15/40; B05B 1/14; B05B 1/34; B65D 2547/06; B65D 2555/00; B65D 25/42; B65D 35/28; B65D 41/20; B65D 47/06
  See application file for complete search history.

(56) References Cited

U.S. PATENT DOCUMENTS

| | | | |
|---|---|---|---|
| 5,056,689 A | 10/1991 | Heyl et al. | |
| 5,154,325 A * | 10/1992 | Ryder | B05B 11/047 222/189.06 |
| 5,499,751 A | 3/1996 | Meyer | |
| 5,588,559 A | 12/1996 | Vallet et al. | |
| 5,681,463 A * | 10/1997 | Shimizu | B01D 61/18 210/266 |
| 5,730,322 A | 3/1998 | Iba et al. | |
| 1,012,390 A1 | 11/2018 | Chauhan et al. | |
| 2004/0074925 A1 | 4/2004 | Faurie | |
| 2006/0243696 A1 | 11/2006 | Spada et al. | |
| 2009/0236445 A1 | 9/2009 | Lintern et al. | |
| 2017/0224531 A1 | 8/2017 | Chauhan et al. | |

OTHER PUBLICATIONS

Ishibashi, et al. Comparison of the short-term effects on the human corneal surface of topical timolol maleate with and without benzalkonium chloride. J Glaucoma. Dec. 2003;12(6):486-90.

Jaenen, et al. Ocular symptoms and signs with preserved and preservative-free glaucoma medications. Eur J Ophthalmol. May-Jun. 2007;17(3):341-9.

Nuzzi, et al. Conjunctiva and subconjunctival tissue in primary open-angle glaucoma after long-term topical treatment: an immunohistochemical and ultrastructural study. Graefes Arch Clin Exp Ophthalmol. Mar. 1995;233(3):154-62.

Rolando, et al. The Effect of Different Benzalkonium Chloride Concentrations on Human Normal Ocular Surface. The Lacrimal System. Kugler and Ghedini, New York 1991, 87-91.

PCT/US2019/026070 International Search Report and Written Opinion dated Aug. 1, 2019.

PCT/US2019/20670 Invitation to Pay Additional Fees dated Jun. 7, 2019.

PCT/US2019/026070 International Preliminary Report on Patentability dated Oct. 6, 2020.

PCT/US2020/025412 International Search Report and Written Opinion dated Aug. 12, 2020.

* cited by examiner

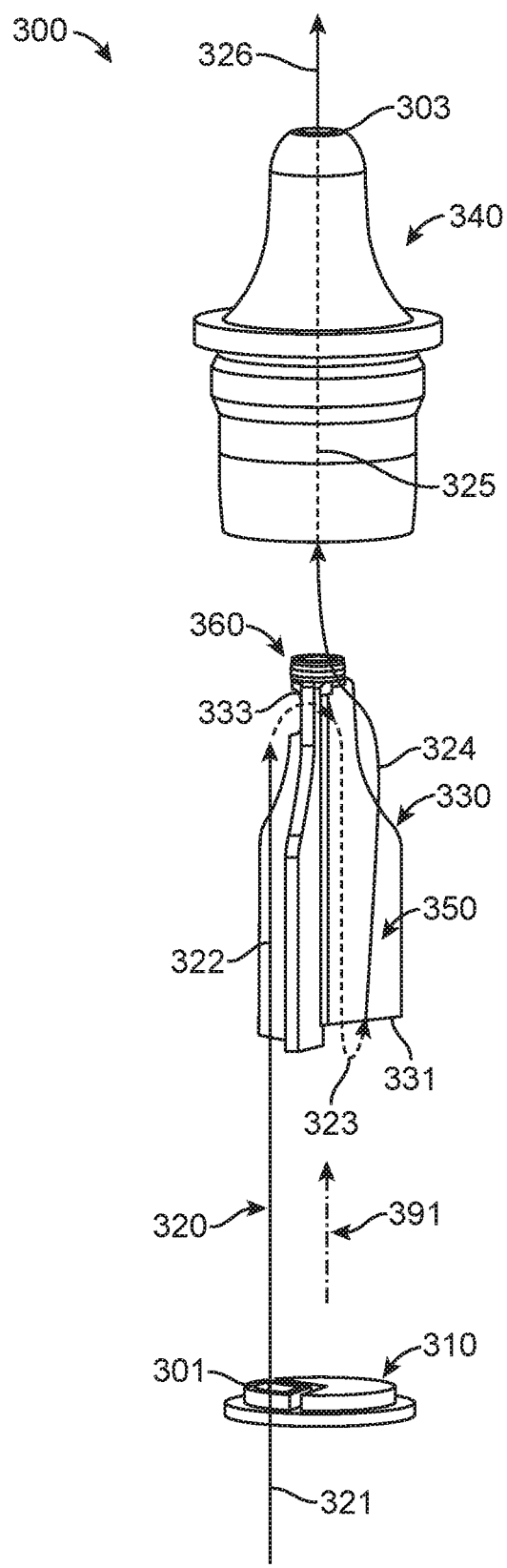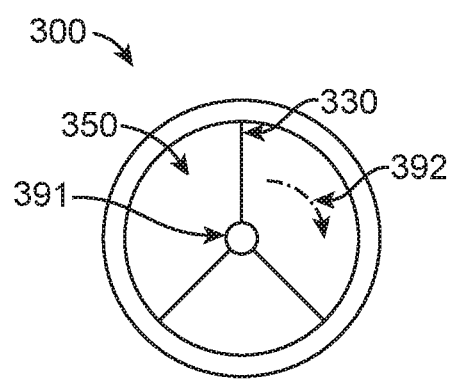
FIG. 3A
FIG. 3B

SYSTEMS AND METHODS FOR DELIVERY OF A THERAPEUTIC AGENT

CROSS REFERENCE

This application claims the benefit of U.S. Provisional Application No. 62/654,089, filed Apr. 6, 2018, and U.S. Provisional Application No. 62/827,743, filed Apr. 1, 2019, both of which are incorporated herein by reference their entireties.

BACKGROUND

The present disclosure generally relates to systems and methods for removal of preservatives and removing a preservative from a fluid comprising a therapeutic agent.

Prior approaches to the removing a preservative from a fluid comprising a therapeutic agent to an eye may be less than ideal in at least some respects. Patients suffering from chronic diseases may use daily eye drop instillations, for example for the treatment of glaucoma. In order to prevent bacterial growth, commercially available eye drop formulations typically use a preservative, in order to address possible bacterial contamination.

Although preservative removal devices have been proposed, the prior approaches can be less than ideal and overly complex in at least some instances. For example some prior approaches can remove either less preservative than would be ideal or more therapeutic agent than would be ideal. Patient compliance with prior eye dropper devices can be less than ideal, and it would be helpful if a device that removes preservatives would be at least as easy to use as the prior devices. However, work in relation to the present disclosure suggests that the amounts of pressure used with prior preservative removal devices can be somewhat greater than would be ideal. Also, as eye drops are typically delivered with a squeeze bottle, the prior approaches to preservative removal can require more pressure than would be ideal for at least some people, e.g. elders.

In light of the above, improved systems and methods for removing a preservative from a fluid comprising a therapeutic agent are desired. Ideally these systems and methods would address at least some of the above drawbacks of the prior approaches, and reduce preservatives in eye drops while substantially retaining the therapeutic agent with very little increase in the amount of bottle pressure to deliver the drops.

SUMMARY

The present disclosure relates to apparatuses and methods for removing a preservative from a fluid comprising a therapeutic agent. The apparatuses can be configured in many ways and may comprise a nozzle configured to deliver the therapeutic agent to an eye with a nozzle. The presently disclosed methods and apparatuses can reduce preservatives in eye drops while substantially retaining the therapeutic agent with very little increase in the amount of bottle pressure to deliver the drops. This can be achieved with a nozzle that fits on the end of a squeeze bottle that allows the drops to be easily delivered. Although reference is made to the treatment of eyes with nozzles coupled to containers, the methods and apparatuses disclosed herein can be configured in many ways to deliver therapeutic agents to many locations of the body, such as with implantable devices, syringes coupled to needles and intravenous drug delivery.

In some embodiments, a porous material is disposed in the squeeze bottle tip and is configured to rapidly and selectively remove the preservative as the fluid comprising a therapeutic agent with preservative flows past. In such embodiments, it may be beneficial to secure the porous material in the tip and to provide a flow path of the drug formulation through the porous material. In some embodiments, a nozzle comprises a flow diverter which directs a flow path from a fluid inlet to a fluid outlet over a length greater than the distance from the inlet to the outlet, which provides an increased interaction of the drug formulation and the porous material in a compact size. The combination of the flow diverter and porous material may enhance the ability to selectively remove the preservative without substantial removal of the therapeutic agent from the drop delivered to the eye, with a nominal increase in pressure as compared with a standard nozzle.

In an aspect, a device for removing a preservative from a formulation comprising a therapeutic agent is provided. The device may comprise: a nozzle comprising: a fluid outlet; an inlet cap comprising one or more apertures, the one or more apertures comprising a fluid inlet, wherein the inlet cap has a hydraulic permeability less than 10 Darcy; and a matrix disposed within the nozzle, wherein the matrix comprises absorbed particles of the preservative and wherein the hydraulic permeability of the inlet cap is less than a hydraulic permeability of the matrix.

In some embodiments, the device further comprises an outlet cap comprising one or more apertures, the one or more apertures comprising the fluid outlet, wherein the outlet cap has a hydraulic permeability less than 10 Darcy. In some embodiments, either of the inlet cap or the outlet cap comprises a screen. In some embodiments, either of the inlet cap or the outlet cap comprises a mesh. In some embodiments, either of the inlet cap or the outlet cap comprises a filter, wherein the filter comprises a pore size of about 0.2 microns. In some embodiments, either of the inlet cap or the outlet cap is prewetted with a preservative. In some embodiments, the nozzle further comprises a flow diverter to divert regions of the fluid flow path in a plurality of different directions, a total distance along the fluid flow path through the matrix from the fluid inlet to the fluid outlet being longer than a distance along an axis from the fluid inlet to the fluid outlet.

In some embodiments, the hydraulic permeability of the inlet cap is about 0.1 Darcy. In some embodiments, the hydraulic permeability of the outlet cap is about 0.1 Darcy. In some embodiments, a pore size of the one or more apertures in the inlet cap or the outlet cap is less than a particle size of the matrix. In some embodiments, a pore size of the one or more apertures in the inlet cap or the outlet cap is about 0.2 microns. In some embodiments, a first drop of the formulation from the device and a tenth drop of the formulation from the device comprise equal concentrations of the preservative to within 10%. In some embodiments, a drop of the formulation from the device dispensed on a first day and a second drop dispensed on a seventh day comprise equal concentrations of the preservative to within 10% at a drop rate of at least one drop per day.

In some embodiments, the formulation is forced through the nozzle from the fluid inlet to the fluid outlet. In some embodiments, forcing the fluid through the nozzle removes a preservative from the formulation. In some embodiments, at least 50 percent of the preservative is removed from the fluid and wherein at least 50 percent of the therapeutic agent is retained. In some embodiments, a squeeze pressure is exerted by a user to form a drop. In some embodiments, the squeeze pressure comprises at least 0.01 Atm. In some embodiments, the squeeze pressure is within a range from 0.01 Atm to 0.5 Atm. In some embodiments, the device further comprises a reservoir containing the formulation and wherein the reservoir has an internal pressure which increases with increasing squeeze pressure. In some embodiments, the internal pressure comprises a pressure within a range from 1 Atm to 5 Atm. In some embodiments, the drop is formed within a time defined by a range between 0.1 seconds and 10 seconds. In some embodiments, the drop comprises a volume defined by a range between 1 µL and 100 µL. In some embodiments, the drop comprises a flow rate defined by a range between 1 µL/min and 1000 µL/min.

In an aspect, a nozzle for removing a preservative from a fluid comprising a therapeutic agent to treat an eye is provided. The nozzle may comprise a fluid inlet configured to receive fluid from a container; a fluid outlet coupled to the inlet, the outlet configured to deliver the fluid comprising the therapeutic agent to the eye; a distance extending along an axis from the fluid inlet to the fluid outlet; a fluid flow path extending from the fluid inlet to the fluid outlet, a porous material along the flow path to selectively remove the preservative; and a flow diverter to divert regions of the fluid flow path in a plurality of different directions, a total distance along the fluid flow path through the porous material from the inlet to the outlet greater than the distance from the fluid inlet to the fluid outlet along the axis.

In some embodiments, the nozzle may include a flow diverter which comprises a plurality of elongate structures to divert the fluid in the plurality of different directions. Optionally, in some embodiments, the nozzle may include a plurality of flow diverters each of which comprises a resistance to flow greater than the porous material located along the flow path. In some embodiments, the nozzle may include a plurality of elongate structures each of which comprises a length oriented in a direction corresponding to at least one of the plurality of directions, a width oriented transversely to said length and at least one of the plurality of directions, and a thickness oriented transversely to said length and said width. Optionally, in some embodiments, a nozzle may include a plurality of elongate structures in which said length, width and thickness are oriented perpendicularly to each other. Optionally, in some embodiments, a nozzle may include a plurality of elongate structures in which said length of said each of the plurality of elongate structures extends a distance of within a range from about 0.5 mm to about 10 mm.

In some embodiments, the nozzle may include a flow path which comprises a circumferential distance about an axis extending between the fluid inlet and the fluid outlet, the nozzle comprising an outer circumference along an outer surface of the nozzle, the circumferential distance corresponding to at least half of the circumference of the nozzle. In some embodiments, the nozzle may include a flow path which substantially reverses direction at least once and optionally which substantially reverses direction at least twice.

In some embodiments, the nozzle may include a flow diverter, which increases the flow path by a factor of at least 1.5 compared to the distance from the fluid inlet to the outlet and optionally wherein the flow diverter increases the flow path by a factor of at least 2.0 and optionally wherein the flow diverter increases the flow path by a factor of at least 2.5 and optionally wherein the flow diverter increases the flow path by a factor of at least 3.0 and optionally wherein the flow diverter increases the flow path by a factor of at least 5.0 and optionally wherein the factor is within a range from 2.0 to 10, 2.5 to 9, 3 to 8, or 5 to 7 and optionally wherein said factor comprises a multiplicative factor.

In some embodiments, the nozzle may include a porous material which comprises a tortuosity and wherein the tortuosity of the porous material combined with the flow diverter increase the flow path in accordance with a multiplicative factor of a first flow path length corresponding to flow defined by the flow diverter and a second flow path length corresponding to the tortuosity of the porous material. In some embodiments, the nozzle may include a flow path which changes from a first direction along a first flow path to a second direction along a second flow path, an angle extending between the first flow path in the first direction and the second flow path in the second direction, the angle comprising at least 90 degrees. Optionally, in some embodiments, the flow path comprises an angle which is within a range from 90 to 180 degrees. Optionally, in some embodiments, the nozzle includes a flow path which substantially reverses direction at least once and optionally reverses direction at least twice.

In some embodiments, the nozzle includes a fluid inlet which comprises an inlet aperture, and a fluid outlet which comprises an outlet aperture with a fluid path extending therebetween. In some embodiments, the nozzle includes an inlet aperture, an outlet aperture and a plurality of flow diverters which are arranged to allow fluid flow through the porous material while retaining the porous material with the flow diverters. Optionally in some embodiments, the nozzle includes an inlet aperture, an outlet aperture and a plurality of flow diverters which are arranged to allow fluid flow through the porous material which comprises a porous polymer matrix. In some embodiments, the nozzle includes an outlet aperture which is configured to allow fluid flow while retaining the porous material.

In some embodiments, the nozzle includes a flow diverter which extends between a first volume of the porous material and a second volume of the porous material in order to selectively direct flow from the first volume to the second volume. In some embodiments, the nozzle includes a flow diverter which comprises at least one interior aperture between the first volume and the second volume. In some embodiments, the nozzle includes a first volume which is fluidically coupled to the inlet aperture and a second volume which is fluidically coupled to the outlet aperture, the second volume downstream from the first volume.

In some embodiments, the nozzle includes an insert configured to fit into a commercially available eyedropper nozzle. In some embodiments, the nozzle includes an insert configured to press fit into the commercially available eyedropper nozzle. In some embodiments, the nozzle comprises an insert which comprises the flow diverter to separate regions of the flow path, a first cap, and a second cap. In some embodiments, the nozzle includes a first cap which comprises an inlet aperture configured to allow fluid flow while retaining the porous material. In some embodiments, the nozzle includes a first cap which is fluidically connected to the fluid inlet. In some embodiments, the nozzle includes a second cap which comprises an outlet aperture configured to allow fluid flow while retaining the porous material. In some embodiments, the nozzle includes a second cap which is fluidically connected to the fluid outlet.

In some embodiments, the nozzle includes a flow diverter configured to separate regions of the flow path and which comprises at least one flow diverter between a first volume of a porous polymer matrix and a second volume of a porous polymer matrix. In some embodiments, the nozzle includes a flow diverter which comprises at least one interior aperture between the first volume and the second volume. In some embodiments, the nozzle includes a first volume fluidically connected to the inlet aperture. In some embodiments, the nozzle includes a second volume fluidically connected to the outlet aperture.

In some embodiments, the nozzle includes a fluid which comprises a solution, emulsion, or suspension comprising a preservative and a therapeutic agent. In some embodiments, the nozzle includes a preservative which comprises BAK. In some embodiments, the nozzle comprises a therapeutic agent which comprises timolol, dorzolamide, dexamethoasone phosphate, dexamethasone, or latanoprost.

In some embodiments, the nozzle includes fluid which is forced through the nozzle via the flow path. In some embodiments, the nozzle includes forcing the fluid through the nozzle which removes a preservative from the fluid. In some embodiments, the nozzle includes a preservative at least 50 percent of which is removed from the fluid and a therapeutic agent at least 50 percent of which is retained.

In some embodiments, the nozzle includes a squeeze pressure which is exerted by a user to form a drop. In some embodiments, the nozzle includes a squeeze pressure which comprises at least 0.01 Atm. In some embodiments, the nozzle includes a squeeze pressure which is within a range from 0.01 Atm to 0.5 Atm. In some embodiments, the nozzle includes a container which has an internal pressure which increases with increasing squeeze pressure. In some embodiments, the nozzle includes an internal pressure which comprises a pressure within a range from 1 Atm to 5 Atm.

In some embodiments, the nozzle includes a drop which is formed within a time defined by a range between 0.1 seconds and 10 seconds. In some embodiments, the nozzle includes a drop which comprises a volume defined by a range between 1 µL and 100 µL. In some embodiments, the nozzle includes a drop which comprises a flow rate defined by a range between 1 µL/min and 1000 µL/min.

In some embodiments, the nozzle includes a container which is a compressible bottle. In some embodiments, the nozzle is configured to provide multiple doses of a therapeutic agent. In some embodiments, the nozzle includes an inlet which is configured to decrease bacterial growth.

In some embodiments, the nozzle includes a porous material which comprises a porous hydrophilic polymeric matrix disposed within the nozzle. In some embodiments, the nozzle includes a matrix which comprises a hydraulic permeability of at least 0.01 Darcy. In some embodiments, the nozzle includes a matrix which comprises a hydraulic permeability of at least 1 Darcy. In some embodiments, the nozzle includes a matrix which is configured to remove a preservative from a solution, emulsion, or suspension. In some embodiments, the nozzle includes a matrix which comprises a partition coefficient for the preservative from the solution, emulsion, or suspension of at least 100. In some embodiments, the nozzle includes a matrix which comprises PHEMA, poly hydroxyl ethyl methacrylate-co-methacrylic acid, or a combination thereof. In some embodiments, the nozzle includes a matrix which is preloaded with a preservative.

In some embodiments, the nozzle includes a porous polymeric matrix which comprises a tortuosity of at least 1.5 to increase the flow path by a multiplicative factor of at least 1.5. In some embodiments, the nozzle includes a porous polymeric matrix which comprises a tortuosity of at least 2.0 to increase the flow path by a multiplicative factor of at least 2.0. In some embodiments, the nozzle includes a porous polymeric matrix which comprises a tortuosity of at least 2.5 to increase the flow path by a multiplicative factor of at least 2.5. In some embodiments, the nozzle includes a porous polymeric matrix which comprises a tortuosity of at least 3.0 to increase the flow path by a multiplicative factor of at least 3.0.

In another aspect a device for compacting a polymer matrix within a nozzle for removing a preservative from a fluid comprising a therapeutic agent to an eye is provided. The compaction device may comprise a handle comprising a proximal end and a distal end, wherein the proximal end is configured to be held by a press, wherein the distal end comprises one or a plurality of protrusions and wherein the protrusions are configured to fit within the nozzle of any one of the preceding claims.

In another aspect a method of removing preservative from a therapeutic agent is provided. The method may comprise receiving a solution comprising the therapeutic agent and a preservative; squeezing a compressible bottle comprising a nozzle for removing a preservative from a fluid comprising the therapeutic agent to an eye, wherein the nozzle comprises a fluid inlet, a fluid outlet, and a flow path extending from the fluid inlet to the fluid outlet; and wherein a flow diverter directs flow of the solution in a plurality of different directions, the flow path greater than the distance from the inlet to the outlet.

In another aspect an apparatus for removing a preservative from a fluid comprising a therapeutic agent to treat an eye is provided. The apparatus may comprise a fluid inlet configured to receive fluid from a container; a fluid outlet coupled to the inlet, the outlet configured to deliver the fluid comprising the therapeutic agent to the eye; a distance extending along an axis from the fluid inlet to the fluid outlet; a fluid flow path extending from the fluid inlet to the fluid outlet, a porous material along the flow path to selectively remove the preservative; and a flow diverter to divert regions of the fluid flow path in a plurality of different directions, a total distance along the fluid flow path through the porous material from the inlet to the outlet greater than the distance from the fluid inlet to the fluid outlet along the axis.

In another aspect, one or more apparatuses and methods described herein are directed to a preservative filtering device. The preservative filtering device may be configured to remove components from eye drop solutions which can be harmful to a patient's eye, including components of preservatives included in eye drop solutions. The filtering device may comprise a nozzle of a multi-dose eye drop solution bottle comprising an opening at a first end configured to permit flow of eye drop solution from within the bottle to a subject, and a second end proximate to the eye drop solution contained within the bottle, and wherein the nozzle comprises positioned therein. The apparatus may additionally comprise a removal agent comprising a zinc-removal agent or a chlorine-removal agent, an inert material, and a screen, wherein the inert material is positioned between the at least one of the zinc-removal agent or the chlorine-removal agent and the screen, and wherein the at least one of the zinc-removal agent or the chlorine-removal agent is positioned proximate or adjacent to the opening.

In some embodiments, the zinc-removal agent may comprise ethylenediaminetetraacetic acid (EDTA). The EDTA may be coated onto a plurality of polystyrene beads and the plurality of polystyrene beads may be positioned within the nozzle. The EDTA may be in crystalline form. In some embodiments, the chlorine-removal agent may comprise activated charcoal. In some embodiments, the inert material may comprise cellulose. The inert material may comprise polystyrene beads. In some embodiments, the removal agent may be position adjacent the opening.

In another aspect, the disclosure provides a multi-dose eye drop solution bottle. In some embodiments, the solution bottle may comprise the preservative filtering device of any of the preceding embodiments.

In an aspect, a flow diverter is provided. The flow diverter may comprise: a fluid inlet, a fluid outlet, and a flow path connecting the fluid inlet to the fluid outlet; wherein the flow diverter comprises at least two interior apertures, wherein the interior apertures connect at least three regions of the flow path, and wherein the flow path substantially changes direction at each of the at least two interior apertures; wherein a matrix is disposed within an interior volume of the flow diverter such that a fluid traversing the flow path flows through the matrix, wherein the fluid comprises a solution, emulsion, or suspension comprising a preservative and a therapeutic agent, wherein the matrix comprises absorbed particles of the preservative from the solution, emulsion or suspension.

In some embodiments, the flow diverter is a part of a nozzle system for delivery of an ophthalmic agent and wherein the nozzle system comprises a nozzle cap. In some embodiments, the flow diverter is removably coupled to an interior of a nozzle of the nozzle system and wherein the flow diverter is secured within the nozzle with a nozzle cap. In some embodiments, the flow diverter is coupled to an interior of a nozzle of the nozzle system and wherein the flow diverter is not removable. In some embodiments, the flow diverter is coupled to an insert and wherein the insert is removably coupled to the interior of a nozzle of the system. In some embodiments, a mesh, a screen, or a filter is disposed between a nozzle cap and a flow diverter. In some embodiments, a mesh, a screen, or a filter is disposed between an outlet of the nozzle and the fluid outlet of the flow diverter. In some embodiments, the at least three regions of the flow path are separated from one another by one or more barriers, wherein the one or more barriers comprise the interior apertures. In some embodiments, the flow path traverses an angular path about an axis of the nozzle.

In an aspect, a flow diverter is provided. The flow diverter may comprise: a fluid inlet, a fluid outlet, and a flow path connecting the fluid inlet to the fluid outlet; wherein the flow diverter comprises a coiled barrier, wherein the flow path traverses an angular path about an axis of the flow diverter and around the coiled barrier, wherein one end of the flow path is at the interior of the coil and wherein an opposite end of the flow path is at the exterior of the coil; wherein a matrix is disposed within an interior volume of the flow diverter such that a fluid traversing the flow path flows through the matrix, wherein the fluid comprises a solution, emulsion, or suspension comprising a preservative and a therapeutic agent, wherein the matrix comprises absorbed particles of the preservative from the solution, emulsion or suspension.

In some embodiments, the flow diverter is a part of a nozzle system for delivery of an ophthalmic agent and wherein the nozzle system comprises a nozzle cap. In some embodiments, the flow diverter is removably coupled to an interior of a nozzle of the nozzle system and wherein the flow diverter is secured within the nozzle with a nozzle cap. In some embodiments, the flow diverter is coupled to an interior of a nozzle of the nozzle system and wherein the flow diverter is not removable. In some embodiments, the flow diverter is coupled to an insert and wherein the insert is removably coupled to the interior of a nozzle of the system. In some embodiments, a mesh, a screen, or a filter is disposed between a nozzle cap and a flow diverter. In some embodiments, a mesh, a screen, or a filter is disposed between an outlet of the nozzle and the fluid outlet of the flow diverter. In some embodiments, the coiled barrier is supported by spacers, the spacers forming a plurality of interior apertures. In some embodiments, the coiled barrier is supported by an interior column.

In an aspect, a flow diverter is provided. A flow diverter may comprise: a fluid inlet, a fluid outlet, and a flow path connecting the fluid inlet to the fluid outlet; wherein the flow diverter comprises at least one inner region and at least one outer region, the at least one inner region being within the at least one outer region, and the at least one inner region and the at least one outer region being fluidically connected; wherein a matrix is disposed within an interior volume of the flow diverter such that a fluid traversing the flow path flows through the matrix, wherein the fluid comprises a solution, emulsion, or suspension comprising a preservative and a therapeutic agent, wherein the matrix comprises absorbed particles of the preservative from the solution, emulsion or suspension.

In some embodiments, the flow diverter is a part of a nozzle system for delivery of an ophthalmic agent and wherein the nozzle system comprises a nozzle cap. In some embodiments, the flow diverter is removably coupled to an interior of a nozzle of the nozzle system and wherein the flow diverter is secured within the nozzle with a nozzle cap. In some embodiments, the flow diverter is coupled to an interior of a nozzle of the nozzle system and wherein the flow diverter is not removable. In some embodiments, the flow diverter is coupled to an insert and wherein the insert is removably coupled to the interior of a nozzle of the system. In some embodiments, a mesh, a screen, or a filter is disposed between a nozzle cap and a flow diverter. In some embodiments, a mesh, a screen, or a filter is disposed between an outlet of the nozzle and the fluid outlet of the flow diverter. In some embodiments, the at least one inner region and the at least one outer region are fluidically connected by a plurality of interior apertures. In some embodiments, the at least one inner region and the at least one outer region are fluidically connected by a plurality of interior apertures. In some embodiments, the apertures are circular or annular.

In any aspect of the flow diverters disclosed herein, the preservative may comprise BAK. In any aspect of the flow diverters disclosed herein, the therapeutic agent may comprise timolol, dorzolamide, dexamethoasone phosphate, dexamethasone, or latanoprost. In any aspect of the flow diverters disclosed herein, the matrix may comprise absorbed particles of the preservative from the fluid. In any aspect of the flow diverters disclosed herein, a flow rate for the fluid through the flow diverter under human applied pressure may be within a range between 1 µL/min and 1000 µL/min.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A illustrates an example nozzle system comprising a removable flow diverter, in accordance with some embodiments.

FIG. 3B illustrates a bottom view of the nozzle system of FIG. 3A, in accordance with some embodiments.

DETAILED DESCRIPTION

Figure 1:
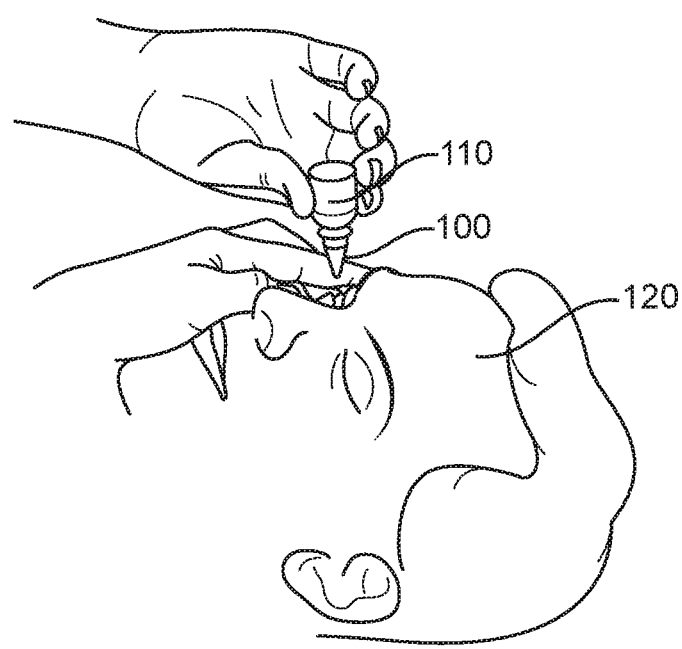
FIG. 1 shows an example user administering an eye drop using a nozzle, in accordance with some embodiments.

The potential for ocular damage from the preservatives may be elevated among patients suffering from chronic diseases which may require daily eye drop instillations for periods of years to decades, such as glaucoma patients. Potential toxic side effects from preservative-free eye drops can be lower than from their preserved counterparts. A multicenter cross-sectional epidemiologic study using preservative or preservative-free beta-blocking eye drops indicated that patients on preservative free eye drops may exhibit fewer ocular symptoms and signs of irritation compared to those using preserved eye drops. (Jaenen et al. "Ocular Symptoms and Signs with Preserved and Preservative-free Glaucoma Medications", European Journal of Ophthalmology. 2007, 17, 341-9) As shown in the referenced study, preserved glaucoma drug timolol may cause higher tear film instability and potentially disrupts corneal barrier function as compared to preservative-free timolol in healthy subjects. (Ishibashi et al., "Comparison of the Short-term Effects on the Human Corneal Surface of Topical Timolol Maleate with and without Benzalkonium Chloride", Journal of Glaucoma, 2003, 12, 486-90) A similar result to Ishibashi et al. was found when comparing preservative-free and BAK-containing carteolol. (Baudouin et al., "Short Term Comparative Study of Topical 2% Carteolol with and without Benzalkonium Chloride in Healthy Volunteers", British Journal of Ophthalmology. 1998, 82, 39-42) Goblet cell loss and increased cytoplasmic/nucleus ratio, two characteristics of dry eye disease, may occur when using BAK containing tear substitutes. (Rolando et al., "The Effect of Different Benzalkonium Chloride Concentrations on Human Normal Ocular Surface". The Lacrimal System, Kugler and Ghedini, New York 1991, 87-91) Reduction in Schirmer test values was observed for subjects receiving BAK eye drops compared with subjects not receiving therapy. (Nuzzi et al., "Conjunctiva and Subconjunctival Tissue in Primary Openangle Glaucoma after Long-term Topical Treatment: an Immunohistochemical and Ultrastructural Study", Graefe's Archive for Clinical and Experimental Ophthalmology, 1995, 233, 154-62) Patients using preserved eye drops and experiencing toxicity symptoms, such as allergy, blepharitis or dry eye, may show improvement upon switching to preservative-free formulations. Such studies suggest a possible role of preservatives in the preponderance of dry eye symptoms in glaucoma patients, who typically use multiple drugs with multiple instillations each day.

The present disclosure relates to apparatuses, systems, and methods for removing a preservative from a fluid comprising a therapeutic agent. The apparatuses and systems can be configured in many ways and may comprise a nozzle configured to deliver the therapeutic agent to an eye with a nozzle. The presently disclosed methods, systems and apparatuses can reduce preservatives in eye drops while substantially retaining the therapeutic agent with very little increase in the amount of bottle pressure to deliver the drops. This can be achieved with a nozzle that fits on the end of a squeeze bottle that allows the drops to be easily delivered. Although reference is made to the treatment of eyes with nozzles coupled to containers, the methods, systems, and apparatus disclosed herein can be configured in many ways to deliver therapeutic agents to many locations of the body, such as with implantable devices, syringes coupled to needles and intravenous drug delivery.

The disclosed methods, systems, and apparatuses may be used in connection with embodiments and examples of the polymeric matrices and therapeutic formulations disclosed U.S. Pat. No. 10,123,904 and International Publication No. WO 2018/102817, which are each incorporated herein by reference in their entirety.

Nozzle

Embodiments of the disclosure are directed to a multi-dosing device and method that reduces, prevents, or eliminates patients' exposure to adverse effects of various preservatives used in eye drop formulations. Methods, systems, and apparatuses described herein can include eye drop bottles, and/or a removable dispenser nozzle configured to couple to commercially available eye drop bottles. Devices, systems, and methods described herein may remove a preservative from a formulation comprising a therapeutic agent. The formulation may comprise any example, embodiment, or variation of the formulations disclosed herein, including any of those formulations disclosed with reference to the following examples in Table 1, Table 2, Table 3, and Table 4. Devices of the present disclosure may comprise multi-dosing devices for ophthalmic formulations. In some examples, the devices of the present disclosure may comprise a nozzle. In some examples, devices of the present disclosure may comprise a dropper bottle.

In some embodiments, the present disclosure may improve upon systems and methods for removing a preservative from a fluid comprising a therapeutic agent to an eye by providing a flow path that maximizes removal of a preservative from solution so as to minimize patient exposure to preservative. Additionally or alternatively, embodiments of the present disclosure may minimize the probability of bacterial growth at the tip of the nozzle, which may minimize bacterial growth elsewhere in the nozzle and/or bottle.

Additionally or alternatively, the nozzle may increase flow path tortuosity, which may increase the flow path through the nozzle. Embodiments of the present disclosure may distribute a preservative removing agent within a nozzle. Embodiments of the present disclosure may reduce overall squeeze pressure to create a drop. Additionally or alternatively, embodiments of the present disclosure may improve regularity of applied squeeze pressure between subsequent squeezes. Additionally or alternatively, the present disclosure may provide an improved multi-dosing device. Embodiments of the present disclosure may decrease the cost of integrating a preservative remover into an eye dropper by providing a nozzle which fits into standard rather than proprietary bottle geometries.

FIG. 1 shows an example user administering an eye drop using a nozzle, in accordance with some embodiments. Embodiments of the present disclosure provide a nozzle for removing a preservative from a fluid comprising a therapeutic agent to an eye. Nozzle 100 may be integrated into bottle 110, which may contain the therapeutic agent of interest. Bottle 110 may be, for example, a squeeze bottle, a dropper bottle, etc. Bottle 110 may be sealed such that the therapeutic agent contained within may be isolated from the environment except by way of nozzle 100. FIG. 1 shows example user 120 administering a drop comprising an therapeutic agent into his or her eye. Bottle 110 and nozzle 100 may be designed such that a user 120 may easily produce a drop. Bottle 110 may be compressible such that user 120 can apply a squeeze pressure to form a drop within 0.1 to 10 seconds of applying pressure.

Figure 2:
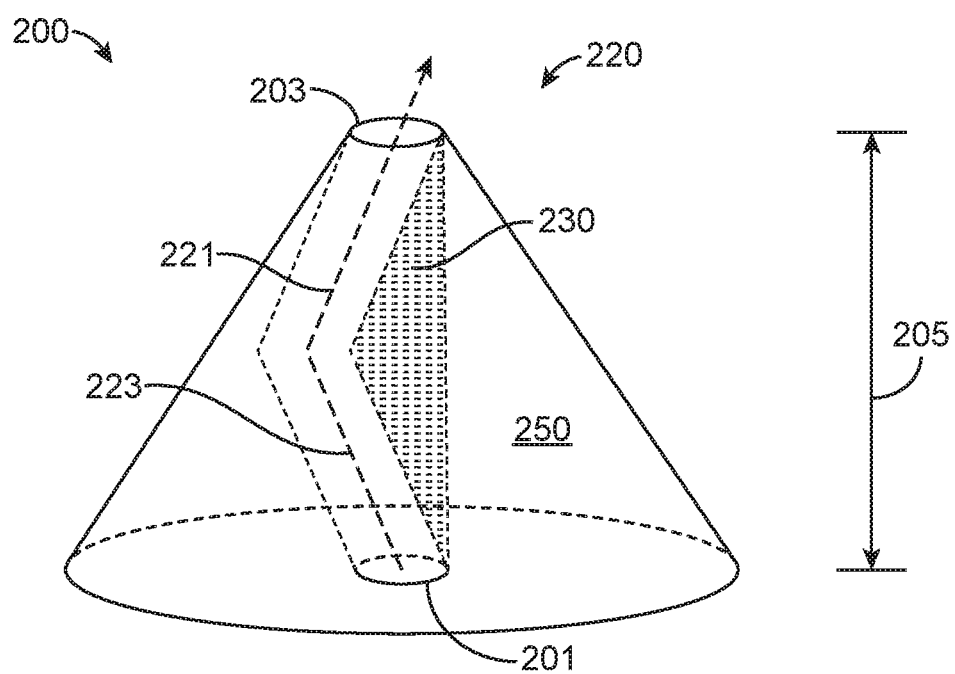
FIG. 2 shows an example nozzle for removing a preservative from a fluid comprising a therapeutic agent to an eye, in accordance with some embodiments.

FIG. 2 shows an example nozzle for removing a preservative from a fluid comprising a therapeutic agent to an eye, in accordance with some embodiments. Shown in FIG. 2, nozzle 200 may be a variation, embodiment, or example of nozzle 100. Nozzle 200 comprises fluid inlet 201 coupled to fluid outlet 203 and a flow path connecting inlet 201 to outlet 203. The fluid inlet may receive fluid from a container such as bottle 110. The fluid outlet may deliver the therapeutic agent to an eye, such as the eye of user 120.

A nozzle of the present disclosure may comprise outlet 203, which may be a fluid outlet. The fluid outlet may allow an ophthalmic formulation of the present disclosure to be delivered to a patient. The outlet may allow a formulation to be delivered to a patient eye. The formulation may be delivered as one or more eye drops. The eye drops may be delivered as part of a dosing regimen or dosage as described elsewhere herein. In some cases the outlet comprises a single aperture. In some cases, the outlet comprises multiple apertures. The outlet may be circular, may be ellipsoid, or may comprise an irregular shape. In embodiments where the outlet is circular or about circular, the outlet may comprise an aperture with a diameter which allows drop formation. For example, the diameter of the outlet may be less than 2 millimeters. The diameter of the outlet may be within a range between 100 microns and 2 millimeters.

In some examples, a nozzle of the present disclosure comprises an outlet cap. An outlet cap may comprise a permeable or semi-permeable barrier between an interior volume of the nozzle and an exterior of the device. In some cases, the outlet cap is gas and liquid permeable. The outlet cap may comprise one or more apertures. The one or more apertures may comprise the fluid outlet 203. In some case, the one or more apertures may be fluidically connected to the fluid outlet. In some embodiments, the outlet cap may comprise a screen, a mesh, or a filter. In some embodiments, the outlet cap comprises a filter, which has a pore size of about 0.2 microns. In some cases, the one or more apertures in the outlet cap may not be the same aperture as the fluid outlet. The one or more apertures in the outlet cap may have an average largest cross-sectional distance of less than 500 microns. The one or more apertures in the outlet cap may have an average largest cross-sectional dimension of less than 100 microns. The one or more apertures in the outlet cap may have an average largest cross-sectional distance of less than 1 micron. The one or more apertures in the outlet cap may have an average largest cross-sectional distance of about 0.2 microns. The size of the one or more apertures in the outlet cap may contribute to the hydraulic permeability of the outlet cap. The outlet cap may have a hydraulic permeability less than 10 Darcy. The outlet cap may have a hydraulic permeability less than 1 Darcy. The outlet cap may have a hydraulic permeability of about 0.1 Darcy. In some examples, a nozzle of the present disclosure does not have an outlet cap.

A formulation may pass through nozzle 200 by traversing an interior volume 250. Interior volume 250 may comprise a material which interacts with the fluid. The material may comprise matrix which may remove preservative from a fluid comprising a therapeutic agent. Nozzle 200 may be designed such that the material may be secured within nozzle 200. For example, the matrix material may be a plug which self-supports between the walls of the interior volume of the nozzle. For example, the plug may be a packed bed of micro-particles. For example, the matrix material may not be self-supporting and may be secured within the interior of the nozzle by way of an inlet cap and an outlet cap. While the present disclosure is directed to removal of a preservative from a therapeutic agent, nozzle 200 may be used for a variety of purposes including, but not limited to, removal of particulate material from eye drops; preventing the entrance of foreign contaminates into a bottle, such as, particulate matter, bacteria or other foreign biological material, chemical contaminates; etc. In some embodiments, the inlet cap is prewetted with a preservative. In some embodiments, a pore size of the one or more apertures in the outlet cap is less than a particle size of the matrix.

The nozzle may additionally comprise a matrix material disposed within an interior of the nozzle. In any embodiment, the matrix material may comprise any embodiment, variation, or example of a preservative removal agent, preservative removing device, a polymeric matrix, or a matrix material as disclosed elsewhere herein. Possible matrix materials which may be used with any embodiment of nozzle of the present disclosure are described further in the section Preservative Removal Agent herein below. A matrix may be disposed within the nozzle. The matrix may remove a preservative from a formulation of the present disclosure. In some examples, the matrix comprises absorbed particles of the preservative.

In some examples, a nozzle of the present disclosure comprises an inlet cap. An inlet cap may comprise a permeable or semi-permeable barrier between an interior volume of the nozzle and a reservoir. In some cases, the inlet cap is gas and liquid permeable. The inlet cap may comprise one or more apertures. The one or more apertures may comprise the fluid inlet 201. In some case, the one or more apertures may be fluidically connected to the fluid inlet. In some embodiments, the inlet cap may comprise a screen, a mesh, or a filter. In some embodiments, the inlet cap comprises a filter, which has a pore size of about 0.2 microns. In some cases, the one or more apertures in the inlet cap may not be the same aperture as the fluid inlet. The one or more apertures in the inlet cap may have an average largest cross-sectional dimension of less than 500 microns. The one or more apertures in the inlet cap may have an average largest cross-sectional dimension of less than 100 microns. The one or more apertures in the inlet cap may have an average largest cross-sectional distance of less than 1 micron. The one or more apertures in the inlet cap may have an average largest cross-sectional distance of about 0.2 microns. The size of the one or more apertures in the inlet cap may contribute to the hydraulic permeability of the inlet cap. The inlet cap may have a hydraulic permeability less than 10 Darcy. The inlet cap may have a hydraulic permeability less than 1 Darcy. The inlet cap may have a hydraulic permeability of about 0.1 Darcy. In some embodiments, the inlet cap is prewetted with a preservative. In some embodiments, a pore size of the one or more apertures in the inlet cap is less than a particle size of the matrix. In some cases, a nozzle of the present disclosure does not comprise an inlet cap.

Fluid may be forced through nozzle 200 via flow path 220. The flow path may be longer than a distance along an axis 205 from the fluid inlet to the fluid outlet. The distance along axis 205 may be less than 10 centimeter (cm). The distance along axis 205 may be less than 5 cm. The distance along axis 205 may be less than 1 cm. The distance along axis 205 may be greater than 1 millimeter. The distance along axis 205 may be greater than 5 millimeter.

Without being limited by theory, it may be beneficial for an inlet cap to have hydraulic permeability that is less than a hydraulic permeability of the matrix. In some cases, the hydraulic permeability of the matrix and the hydraulic permeability of the inlet or outlet cap may be about equal. In some cases, an inlet cap or an outlet cap may have a hydraulic permeability which is less than the hydraulic permeability of the matrix. The force behind the fluid may comprise a pressure differential, such as a squeeze pressure. The formulation may be forced through the nozzle from the fluid inlet to the fluid outlet. In some embodiments, forcing the fluid through the nozzle removes a preservative from the formulation. In some embodiments, at least 50 percent of the preservative is removed from the fluid and wherein at least 50 percent of the therapeutic agent is retained.

For example, it may be beneficial for a squeeze pressure to be small enough that an elder may be capable of squeezing a device for removing a preservative, such as a compressible bottle. In some embodiments, a squeeze pressure is exerted by a user to form a drop. In some embodiments, the device further comprises a reservoir containing the formulation and wherein the reservoir has an internal pressure which increases with increasing squeeze pressure. In some embodiments, the squeeze pressure comprises at least 0.01 Atm. In some embodiments, the squeeze pressure is within a range from 0.01 Atmospheres (Atm) to 0.5 Atm. In some embodiments, the internal pressure comprises a pressure within a range from 1 Atm to 5 Atm.

In some embodiments, the drop is formed within a time defined by a range between 0.1 seconds and 10 seconds. In some embodiments, the drop is formed with 2 seconds. In some embodiments, the drop comprises a volume defined by a range between 1 microliter (μL) and 100 μL. A volume of a drop may be about 50 μL. In some embodiments, the drop comprises a flow rate within a range between 1 μL/minute and 1000 μL/minute. In some embodiments, a typical flow rate may be 500 μL/minute.

In some embodiments, a first drop of the formulation from the device and a tenth drop of the formulation from the device comprise equal concentrations of the preservative to within 10%. In some embodiments, a drop of the formulation from the device dispensed on a first day and a second drop dispensed on a seventh day comprise equal concentrations of the preservative to within 10% at a drop rate of at least one drop per day.

In some embodiments, a nozzle may comprise one or more of a screen, a mesh, or a filter, such as for example, within an inlet cap or an outlet cap. An inlet cap or an outlet cap may comprise the same materials or different materials. A screen may comprise a metal mesh, such as from woven metal fibers. A filter may be a paper, cloth, or a fibrous filter. In some cases, a screen, a mesh, or a filter is a chemically inert material. For example, an inert material may be silica gel, alumina, glass, cellulose, paper, polystyrene beads, or another inert material.

In other cases, the filter comprises a material selected to absorb a component of the formulation. In some embodiments, the filter comprises a chlorine-removal agent comprising desired affinity for the chlorine-containing component of the preservative such that a desired quantity of the chlorine-containing component can be removed from the eye drop solution as the solution passes over the material in the preservative removing device. The chlorine-removal agent can be configured to have selective affinity for the chlorine-containing component. In some embodiments, the chlorine-removal agent comprises one or more agents configured to trap chlorine. For example, the chlorine-removal agent may be configured to adsorb to free chlorines. In some embodiments, the chlorine-removal agent comprises activated charcoal.

Referring to FIG. 2, nozzle 200 may comprise a flow diverter 230, which may direct the flow path such that fluid flows in a plurality of different directions. The flow path may comprise a plurality of regions, for example, region 221 and region 223, which together may comprise flow path 220 from the inlet to the outlet. As shown in FIG. 2, flow diverter 230 may divert a flow path such that separate regions of the flow path 221 and 223 may be formed. The flow diverter may divert a flow path such that the total distance traversed by the fluid may be longer than the distance 205 from inlet 201 to outlet 203 without the diverter. In some embodiments, the flow diverter may increase the flow path by a factor of at least 1.5. Alternatively, the flow path may increase by a factor of at least 1.1, at least 1.25, at least 1.75, at least 2, at least 2.5, at least 3, at least 4, at least 5, at least 6, at least 7, at least 8, at least 9, at least 10, or by a factor within a range defined by any two of the preceding values.

A flow diverter may improve upon devices without a flow diverter my increasing a path from the fluid inlet to the fluid outlet. The increased path length may limit flow between an inlet and an outlet when the device is not being used. The increased path length may increase a diffusion time for molecules of a preservative to diffuse from an inlet to an outlet. The increased path length may increase a concentration gradient between the inlet and the outlet. In some cases, portions of the device near the outlet may remain substantially preservative free for the working lifetime of the device.

FIG. 3A, FIG. 3B, FIG. 4, and FIG. 5 illustrate example nozzle systems 300, 400, and 500 for integrating a flow diverter 203 into the nozzle for removing a preservative from a fluid comprising a therapeutic agent to an eye. In some examples, an inlet cap and an outlet cap may be parts of or may be integrated with a flow diverter 203 of the following examples. Example nozzle systems may comprise inserts to fit into a tip of standard bottle. In embodiments where the nozzle comprises an insert, the insert may be press fit, glued, welded, compression fit, and/or comprise retention members to fit into a standard bottle. Additionally or alternatively, example nozzle systems comprise caps which may be configured to fit into the mouth of a standard bottle. Additionally or alternatively, example nozzle systems may comprise a proprietary bottle.

In some embodiments, the nozzle may be incorporated into an eye drop dispensing system, which system may comprise a squeezable bottle. A squeezable bottle may comprise a reservoir in which a fluid may be stored. The bottle may be made of a material with sufficiently elastic sidewalls such that the side walls of the bottle may be deform when depressed and substantially recover its original shape when released. When the pressure on the side walls of the bottle increases, the pressure inside the reservoir may increase. The increase in pressure inside of the reservoir may force a liquid through the nozzle and result in drop formation at the tip. The flow of liquid out of the bottle may result in a decrease in pressure within the bottle.

FIG. 3A illustrates example nozzle system 300 comprising removable flow diverter 330, in accordance with some embodiments. Example nozzle system 300 may comprise four parts: inlet cap 310, flow diverter 330, outlet cap 360, and nozzle housing 340. Nozzle system 300 may comprise a matrix 350 disposed within the volume of the nozzle system. Inlet cap 310 may comprise fluid inlet 301. Inlet cap 310 may be made of a material which may be impermeable to fluid. In such embodiments, inlet cap 310 may comprise an inlet aperture, which may be operatively connected to a fluid inlet 301 to receive fluid from a container. The inlet aperture may be open; alternatively, the inlet aperture may comprise a mesh or a screen, such that a matrix material within the nozzle system may be retained by the nozzle system. Inlet cap 310 may be removable such that the nozzle system may be filled with a matrix 350. Outlet cap 360 may comprise an outlet aperture, which may be operably connected to a fluid outlet 303 to deliver the therapeutic agent to the eye. The outlet aperture may be open; alternatively, the outlet aperture may comprise a mesh or a screen, such that a matrix material within the nozzle system may be retained by the nozzle system. Outlet cap 360 may be removable such that the nozzle system may be easily constructed. Alternatively, outlet cap 360 may be molded to flow diverter 330.

Nozzle system may comprise a removable flow diverter 330. Flow diverter 330 may be made of a fluid impermeable material. In some embodiments, flow diverter 330 has a "dart" shape wherein each "wing" of the "dart" separates a region of the flow path 320. Flow diverter 330 may fit snuggly within nozzle housing 340 such that fluid does not ordinarily flow radially between wings of the dart, except where connected by interior aperture 333. The inlet side of flow diverter 330 may fit snuggly with inlet cap 310, such that fluid does not ordinarily flow between wings of the dart and the inlet cap, except where connected by interior aperture 331.

Flow path 320 through nozzle system 300 may comprise regions 321, 322, 323, 324, 325, and 326. Flow path region 321 may pass through inlet cap 310. Flow path regions 322, 323, and 324 may pass through each of three volumes separated by wings of the flow diverter 330. Flow path regions 322, 323, and 324 may direct the flow radially or circumferentially around an axis 391 from the fluid inlet to the fluid outlet of the nozzle system. Flow path region 322 may direct fluid from the inlet aperture toward the nozzle tip in through a first volume of a matrix 350. Flow path region 322 and flow path region 323 may be connected by interior aperture 333. Flow path region 323 may direct fluid from interior aperture 333 toward inlet cap 310 through a second volume of a matrix 350. The flow path 320 may reverse direction a first time at interior aperture 333. Flow path region 323 and flow path region 324 may be connected by interior aperture 331. Flow path region 324 may direct fluid from interior aperture 331 to outlet cap 360 through a third volume of a matrix 350.

The flow path 320 may reverse direction a second time at interior aperture 331. In the illustrated embodiment, flow path path region 325 may direct fluid through nozzle housing 340 toward fluid outlet 303. Flow path region 326 may direct fluid through fluid outlet 303 toward a patient eye.

FIG. 3B illustrates a bottom view of nozzle system 300 also shown in FIG. 3A, in accordance with some embodiments. The nozzle system comprises a central axis 391 extending from a fluid inlet to a fluid outlet. The flow diverter 330 may divide the nozzle system into three regions of the flow path. As the flow path moves from region to region flow is directed radially or circumferentially around the axis 391. Angular path 392 is shown in the illustrated embodiment. Angular path 392 may comprise a radial distance sweeping an angle of 120 degrees around axis 391. Alternatively, angular path 392 may comprise an angle of 1 degrees, 2 degrees, 5 degrees, 10 degrees, 20 degrees, 30 degrees, 60 degrees, 90 degrees, 120 degrees, 180 degrees, 270 degrees, 360 degrees, or any angle within a range defined by any two of the preceding values.

Alternative embodiments of nozzle system 300 may comprise a flow diverter with a "dart" configuration with a greater number of "wings" and with a substantially similar geometry to the illustrated embodiment. Alternative embodiments may comprise for example, 5, 7, 9, 11, 13, 15, 29, 51, 101, 1001, or any odd number of wings within a range defined by any two of the preceding values. A flow path 320 may substantially reverse direction at least 2 times, at least 4 times, for example, at least, 6, 8, 10, 12, 16, 20, 50, 100, 1000, or any even number of times within a range between any two of the preceding values.

Figure 4:
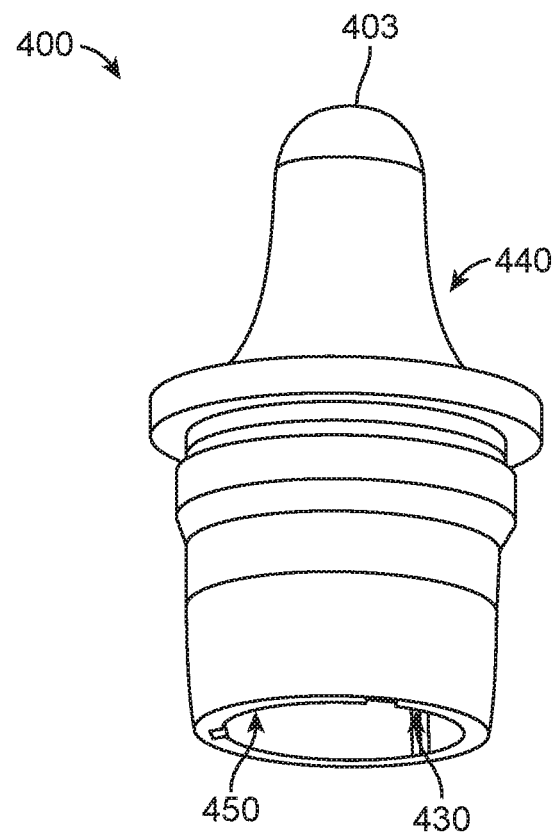
FIG. 4 illustrates an example nozzle system comprising an integrated flow diverter, in accordance with some embodiments.
Figure 4:
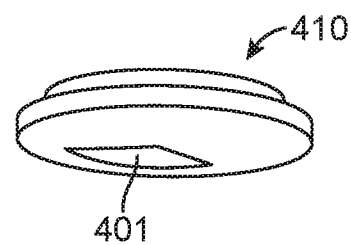

FIG. 4 illustrates example nozzle system 400 comprising an integrated flow diverter 430, in accordance with some embodiments. Example nozzle system 400 may comprise a substantially similar flow path to flow path 320. While flow diverter 330 in FIG. 3A may be removable, flow diverter 430 may be integrated into nozzle tip 440 such that nozzle tip 440 may comprise a single part. Nozzle system 400 may comprise a matrix 450 disposed within the volume of the nozzle system. Nozzle system 400 may comprise an inlet cap 410. Inlet cap 410 may comprise fluid inlet 401. Inlet cap 410 may be made of a material which may be impermeable to fluid. In such an embodiment, inlet cap 410 may comprise an inlet aperture, which may be operatively connected to a fluid inlet 401 to receive fluid from a container. The inlet aperture may be open; alternatively, the inlet aperture may comprise a mesh or a screen, such that a matrix material within the nozzle system may be retained by the nozzle system. Inlet cap 410 may be removable such that the nozzle system may be filled with a matrix 450. Nozzle tip 440 may comprise an outlet aperture, which may be operably connected to a fluid outlet 403 to deliver the therapeutic agent to the eye. The outlet aperture may be open; alternatively, the outlet aperture may comprise a mesh or a screen, such that a matrix material within the nozzle system may be retained by the nozzle system. Nozzle tip 440 may fit into a standard squeeze bottle. Additionally or alternatively, nozzle tip 440 may fit into a proprietary bottle.

Figure 5:
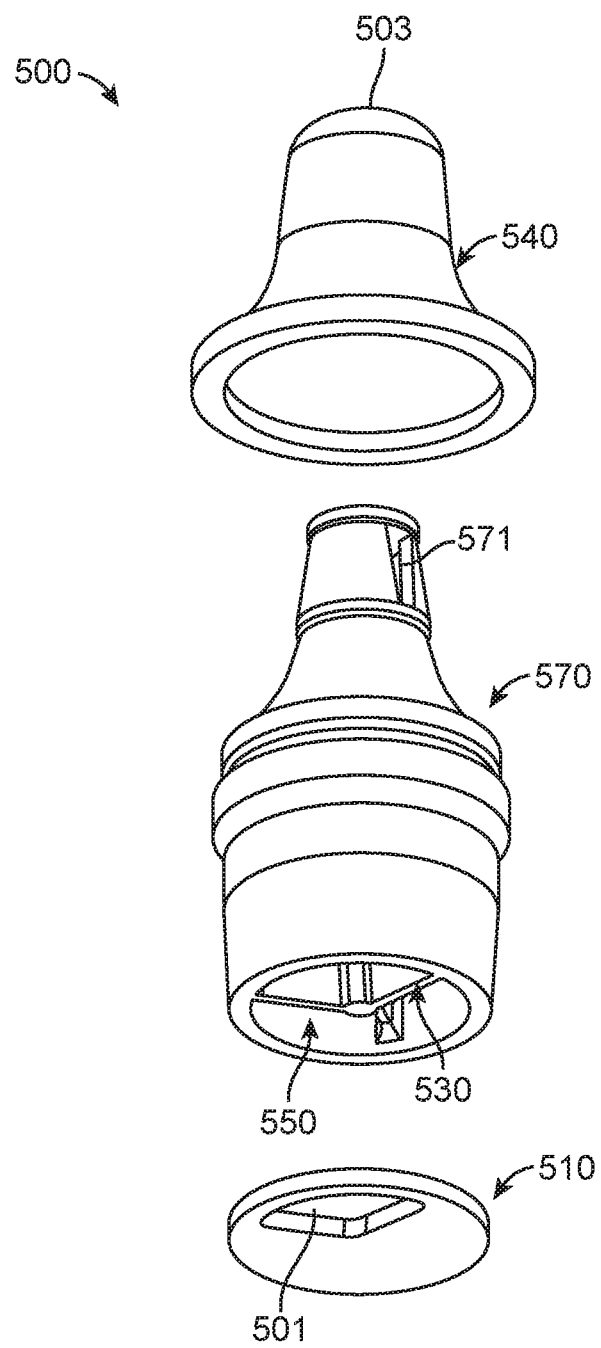
FIG. 5 illustrates an example nozzle system comprising an insert configured to fit into a nozzle tip, in accordance with some embodiments.

FIG. 5 illustrates example nozzle system 500 comprising insert 570 configured to fit into nozzle tip 540, in accordance with some embodiments. Example nozzle system 500 may comprise a substantially similar flow path to flow path 320. Flow diverter 530 may be integrated into insert 570 such that insert 570 may be a single part. Insert 570 may fit snuggly into nozzle tip 540 such that fluid does not ordinarily flow between insert 570 and nozzle tip 540, except via interior aperture 571. Interior aperture 571 may be operably connected to fluid outlet 503, such that fluid may flow from interior aperture 571 to a patient eye. Fluid outlet 503 may be open; alternatively, the outlet may comprise a mesh or a screen, such that a matrix material within the nozzle system may be retained by the nozzle system. Nozzle system 500 may comprise a matrix 550 disposed within the volume of the nozzle system. Nozzle system 500 may comprise an inlet cap 510. Inlet cap 510 may comprise fluid inlet 501. Inlet cap 510 may be made of a material which may be impermeable to fluid. In such embodiments, inlet cap 510 may comprise an inlet aperture, which may be operatively connected to a fluid inlet 501 to receive fluid from a container. The inlet aperture may be open; alternatively, the inlet aperture may comprise a mesh or a screen, such that a matrix material within the nozzle system may be retained by the nozzle system yet allow sufficient fluid flow for drop formation. Inlet cap 510 may be a filter. Inlet cap 510 may be removable such that the nozzle system may be filled with a matrix 550. Nozzle system 500 may fit into a standard squeeze bottle. Additionally or alternatively, nozzle system 500 may fit into a proprietary bottle.

Nozzle systems 300, 400, and 500 comprise examples of integrating a flow diverter into a nozzle using a "dart" geometry flow diverter; however, many possible flow diverter geometries may be integrated into nozzle systems 300, 400, and 500. FIG. 6A, FIG. 6B, FIG. 7A, FIG. 7B, FIG. 8A, FIG. 8B, FIG. 9, FIG. 10, FIG. 11, FIG. 12, FIG. 13, and FIG. 14 illustrate examples, variations, and embodiments of flow diverter geometries, each of which may be integrated into nozzle systems of the present disclosure.

Figure 6A:
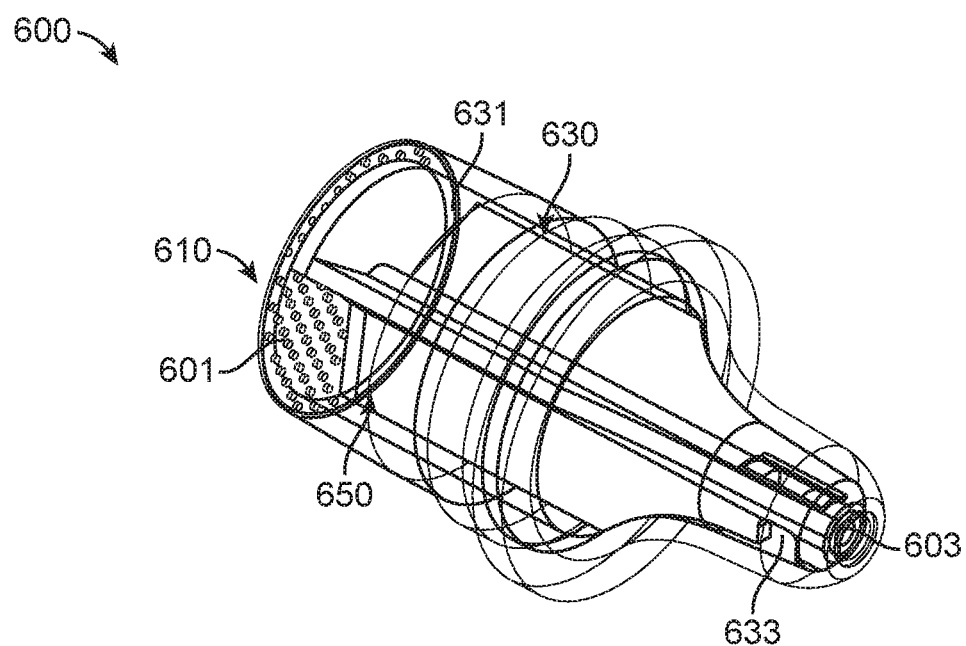
FIG. 6A illustrates a three-dimensional assembly view of a flow diverter with a "dart" geometry integrated into a nozzle, in accordance with some embodiments.
Figure 6B:
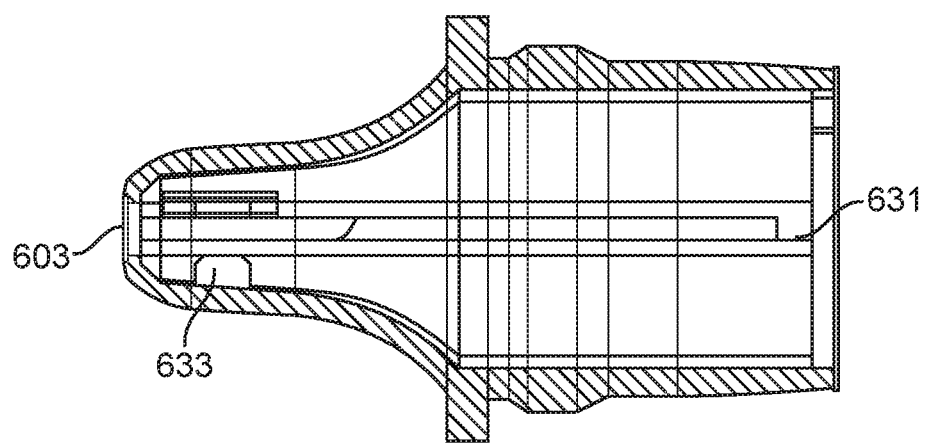
FIG. 6B illustrates a cross-section view of a flow diverter with a "dart" geometry integrated into a nozzle, in accordance with some embodiments.

FIG. 6A illustrates a three-dimensional assembly view of a flow diverter comprising a "dart" geometry integrated into a nozzle, in accordance with some embodiments. FIG. 6B illustrates a cross-section view of a flow diverter with a "dart" geometry integrated into a nozzle, in accordance with some embodiments. Dart geometry 600 may comprise a flow path substantially similar to flow path 320 connecting a fluid inlet 601 to a fluid outlet 603. Dart geometry 600 may be integrated into a nozzle using nozzle systems 300, 400, and 500 described herein. Dart geometry 600 may comprise a flow diverter 630, which may comprise a similar construction to flow diverter 330, which may separate regions of the flow path through volume of matrix material 650. In the illustrated embodiment, the nozzle may comprise inlet cap 610 comprising a mesh screen. The mesh screen may comprise a plurality of inlet apertures, which apertures may comprise fluid inlet 601. Dart geometry 600 may comprise a plurality of interior apertures 631 and 633, which may comprise varying sizes and shapes. Sizes and shapes of the interior apertures may be tuned to optimize drop formation.

Figure 7A:
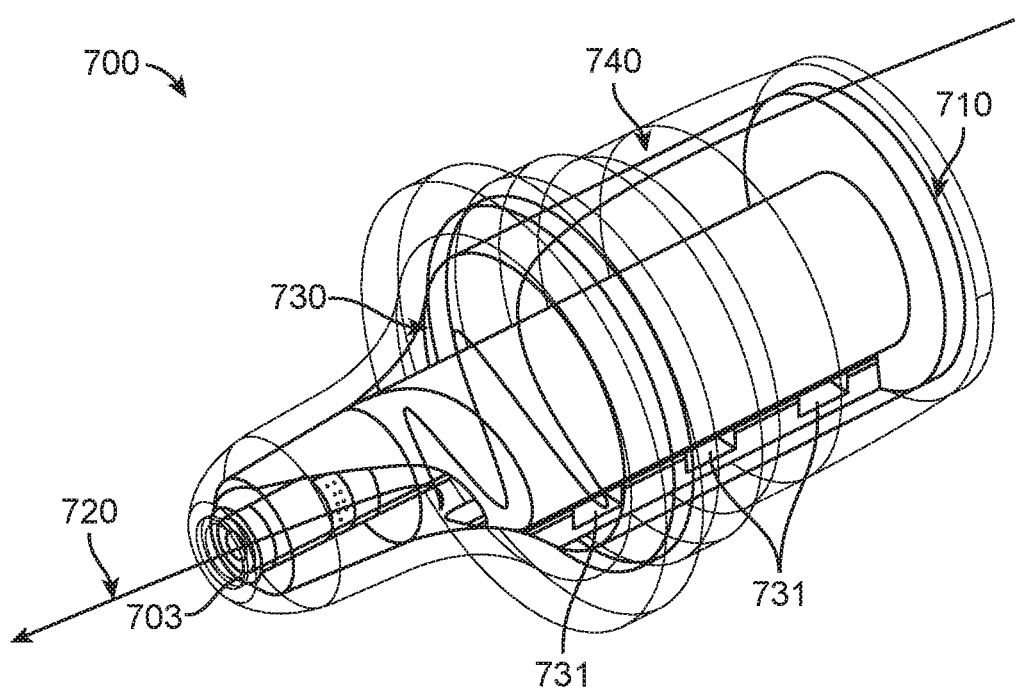
FIG. 7A illustrates a three-dimensional assembly view of a flow diverter with a "nautilus" geometry integrated into a nozzle, in accordance with some embodiments.
Figure 7B:
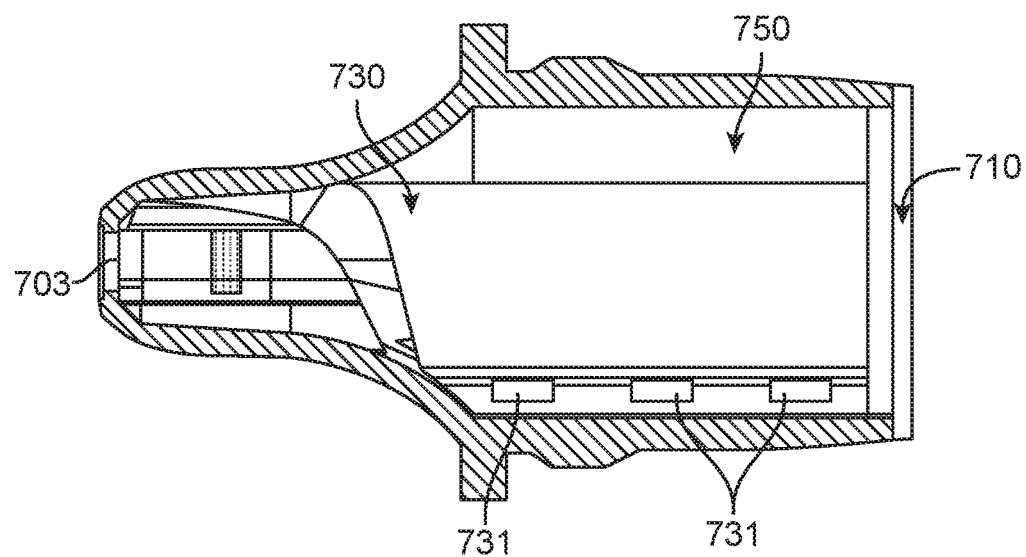
FIG. 7B illustrates a cross-section view of a flow diverter with a "nautilus" geometry integrated into a nozzle, in accordance with some embodiments.

FIG. 7A illustrates a three-dimensional assembly view and FIG. 7B illustrates a cross-section view of a flow diverter comprising a "nautilus" geometry integrated into a nozzle, in accordance with some embodiments. Nautilus geometry 700 may comprise a flow path 720, which may proceed from a fluid inlet 701 to a fluid outlet 703. A nozzle may comprise nozzle housing 740 and flow diverter 730. Geometry 700 may be integrated into a nozzle using nozzle systems 300, 400, and 500 described herein. A nozzle may comprise a matrix 750 disposed therein. Flow path 720 may proceed from an exterior of a nozzle toward an interior of a nozzle by flow path that spirals inward toward the center of the nozzle. The center of the spiral may be operatively connected to fluid outlet 703. Flow diverter 730 may comprise a plurality of interior apertures 731. Dividers between interior apertures may serve to support the walls of flow diverter 730. Additionally or alternatively, the interior apertures may serve to create multiple distinct pathways through the nozzle. In the illustrated embodiment, the nozzle may comprise an inlet cap 710. Inlet cap 710 may comprise substantially similar characteristics to inlet caps of the described herein. Inlet cap may comprise fluid inlet 701. In the illustrated embodiment, flow path 720 may comprise 4 loops around the central axis of the nozzle; alternatively, the flow path may comprise, for example, 1, 2, 5, 10, 20, 50, 100, 200, 500, 1000 loops or a number of loops comprising a number within a range defined by any two of the preceding values.

Figure 8A:
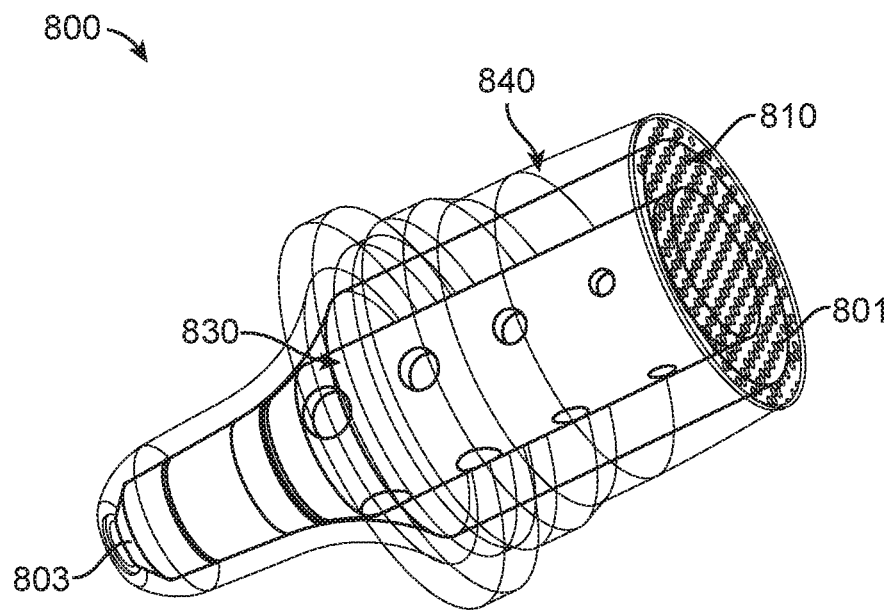
FIG. 8A illustrates a three-dimensional assembly view of a flow diverter with a "concentric" geometry integrated into a nozzle, in accordance with some embodiments.
Figure 8B:
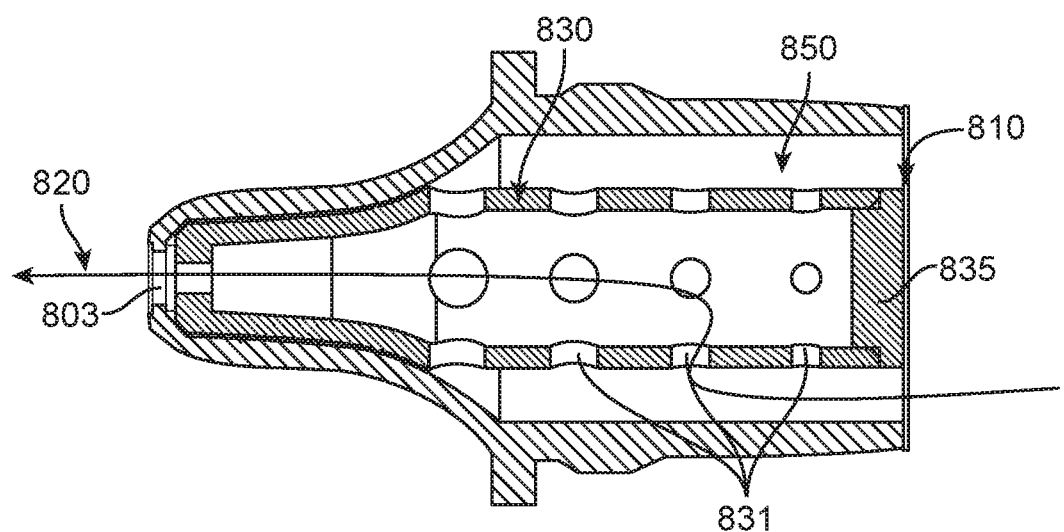
FIG. 8B illustrates a cross-section view of a flow diverter with a "concentric" geometry integrated into a nozzle, in accordance with some embodiments.

FIG. 8A illustrates a three-dimensional assembly view and FIG. 8B illustrates a cross-section view of a flow diverter comprising a "concentric" geometry integrated into a nozzle, in accordance with some embodiments. Concentric geometry 800 may be utilized with two matrix materials (e.g. one type in an interior portion and one type in an annular portion) or with a single matrix material. Concentric geometry 800 may comprise a flow path 820, which may proceed from one or a plurality of fluid inlets 801 to a fluid outlet 803. A nozzle may comprise nozzle housing 840 and flow diverter 830. Geometry 800 may be integrated into a nozzle using nozzle systems 300, 400, and 500 described herein. A nozzle may comprise a matrix 850 disposed therein. Flow diverter 830 may comprise a central lumen with a plurality of interior apertures 831. The plurality of interior apertures may connect concentric annular regions of the nozzle. Flow diverter 830 may additionally comprise bottom 835, which may be impermeable to liquid such that fluid may not ordinarily flow between bottom 835 and the sides of flow divert 830. Flow path 820 may proceed from inlet cap 810, which may comprise the one or plurality of fluid inlets 801, through at least one of the interior apertures 831, toward fluid outlet 803. Inlet cap 810 may comprise substantially similar characteristics to inlet caps of the described herein. In the illustrated embodiment, the flow diverter separates regions of the flow path into two concentric annuli; alternatively, in some embodiments, the flow diverter may separate regions of the flow path into, for example, 1, 2, 5, 10, 20, 50, 100, 200, 500, 1000 concentric annuli, or a number of annuli within a ranged defined by any two of the preceding values.

Figure 9:
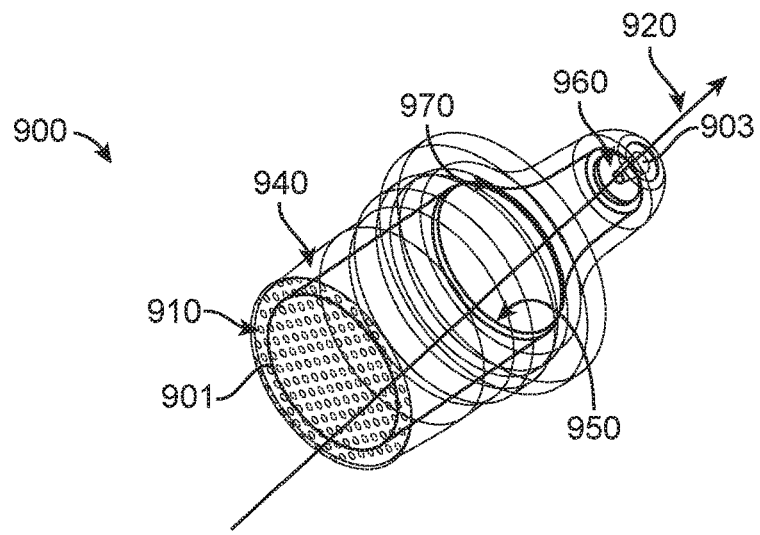
FIG. 9 illustrates a slice through a flow diverter with a "sachet" geometry integrated into a nozzle, in accordance with some embodiments.

FIG. 9 illustrates a slice through a flow diverter with a "sachet" geometry integrated into a nozzle, in accordance with some embodiments. Sachet geometry 900 may comprise a flow path 920, which may proceed from one or a plurality of fluid inlets 901 to a fluid outlet 903. A nozzle may comprise nozzle housing 940 and flow diverter 930. Geometry 900 may be integrated into a nozzle using nozzle systems 300, 400, and 500 described herein. In the illustrated embodiment, the nozzle may comprise inlet cap 910 comprising a mesh screen. The mesh screen may comprise a plurality of inlet apertures, which apertures may comprise fluid inlet 901. In the illustrated embodiment, the nozzle may additionally comprise outlet cap 960 comprising a mesh screen. The mesh screen may comprise a plurality of outlet apertures, which outlet apertures may be operatively connected to fluid outlet 903. Inlet cap 910 and outlet cap 960 may comprise the top and bottom respectively of insert 970. Insert 970 may comprise a matrix 950 disposed therein. A flow path 920 may proceed from the one or a plurality of fluid inlets 901 to a fluid outlet 903. In some embodiments, sachet geometry 900 may be configured to fit within a commercially available nozzle assembly.

Figure 10:
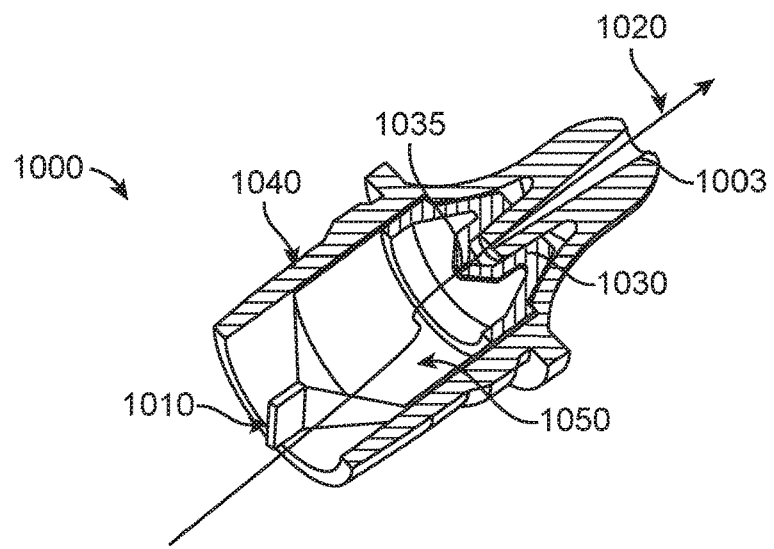
FIG. 10 illustrates a slice though a flow diverter comprising a restriction integrated into a nozzle, in accordance with some embodiments.

FIG. 10 illustrates a slice though a flow diverter comprising a restriction integrated into a nozzle, in accordance with embodiments. Geometry 1000 may comprise a flow path from a fluid inlet in inlet cap 1010 to fluid outlet 1003. A nozzle may comprise a flow diverter 1030 comprising restriction 1035. Geometry 1000 may be integrated in to a nozzle using nozzle systems 300, 400, and 500 described herein. In the illustrated embodiment, the nozzle may comprise inlet cap 1010. In some embodiments, inlet cap 1010 comprises a mesh screen. The mesh screen may comprise a plurality of inlet apertures, which apertures may comprise on or a plurality of fluid inlets. Inlet cap 1010 may be shaped to compress a matrix material. The nozzle may comprise nozzle housing 1040, which may comprise a matrix 1050 disposed therein. The restriction 1035 may be sized and shaped configured to improve the formation of a drop, to improve fluid flow, to improve squeeze pressure, etc.

Figure 11:
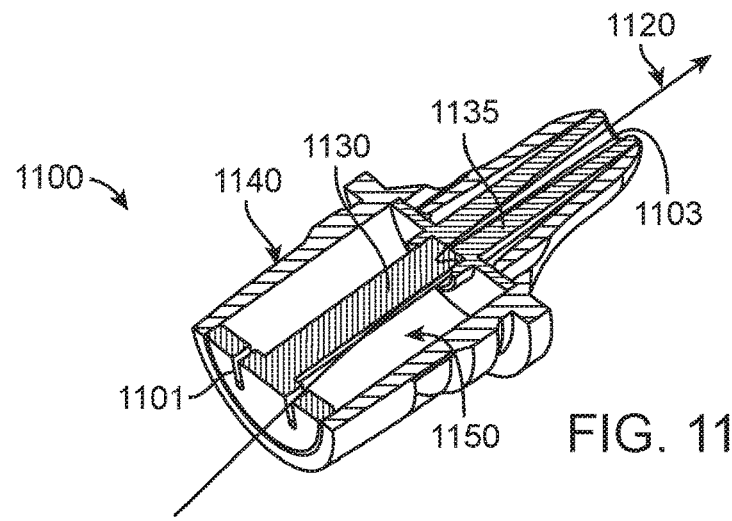
FIG. 11 illustrates a slice through a flow diverter comprising two axially separate inlet orifices integrated into a nozzle, in accordance with some embodiments.

FIG. 11 illustrates a slice through a flow diverter comprising two axially separate inlet orifices integrated into a nozzle, in accordance with some embodiments. Geometry 1100 may comprise a flow path 1120, which may proceed from each or both of the two axially separate inlet orifices 1101 to a fluid outlet 1103. A nozzle may comprise a flow diverter 1130. A nozzle may comprise a matrix 1150 disposed therein. Geometry 1100 may be integrated into a nozzle using nozzle systems 300, 400, and 500 described herein. Geometry 1100 may comprise nozzle insert 1135 disposed within nozzle housing 1140. Nozzle insert 1135 may be configured to improve the formation of a drop by controlling the size of the restriction on the outlet side of nozzle insert 1135, by controlling the insert surface characteristics to change fluid surface tension, and/or to improve fit with a fluid diverter 1130. A flow path 1120 may proceed from two axially separate inlet orifices within an annulus of matrix material around a central flow diverter column to a fluid outlet 1103. In the illustrated embodiment, geometry 1100 comprises two axially separate inlet orifices. Additionally or alternatively, geometry 1100 may comprise 2, 5, 10, 20, 50, 100, 200, 500, 10000, 100000, or 1000000 inlet orifices or a number of inlet orifices within a range defined by any two of the preceding values. In some embodiments, an inlet orifice may comprise a ring shaped opening around a central column. In some embodiments, an inlet orifice comprises a more complex shape. In some embodiments, an inlet orifice may be sized and shaped to optimize flow through the matrix material.

Figure 12:
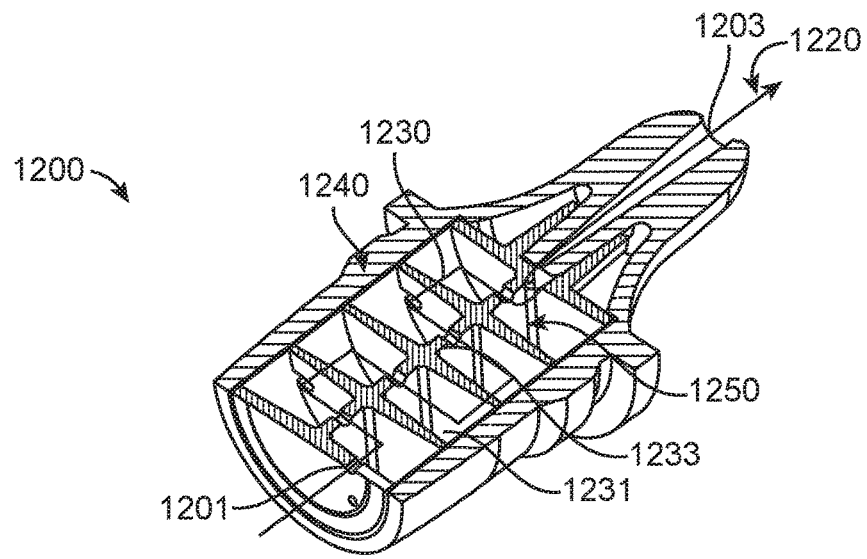
FIG. 12 illustrates a slice through a flow diverter with a "stacked disc" geometry integrated into a nozzle, in accordance with some embodiments.

FIG. 12 illustrates a slice through a flow diverter comprising a "stacked disc" geometry integrated into a nozzle, in accordance with some embodiments. Stack disc geometry 1200 may comprise a flow path 1220, which may proceed from a fluid inlet 1201 to a fluid outlet 1203. A nozzle may comprise nozzle housing 1240 and flow diverter 1230. Geometry 1200 may be integrated into a nozzle using nozzle systems 300, 400, and 500 described herein. A nozzle may comprise a matrix 1250 disposed therein. Flow path 1220 may proceed from an inlet end of a nozzle to an outlet end of a nozzle by sequentially traversing a series of stacked discs, which discs may be filled with a matrix material. The nozzle may comprise interior apertures 1231, which may connect neighboring discs on the axis upon which the discs may be stacked. The nozzle may additionally comprise interior apertures 1233, which may assure that both hemispheres of each disc may be traversed by the fluid. In the illustrated embodiment, flow path 1220 comprises four stacked discs. In some embodiments, a flow path 1220 may comprise 2, 5, 10, 20, 50, 100, 200, 500, 1000 discs or a number of discs within a range defined by any two of the preceding values.

Figure 13:
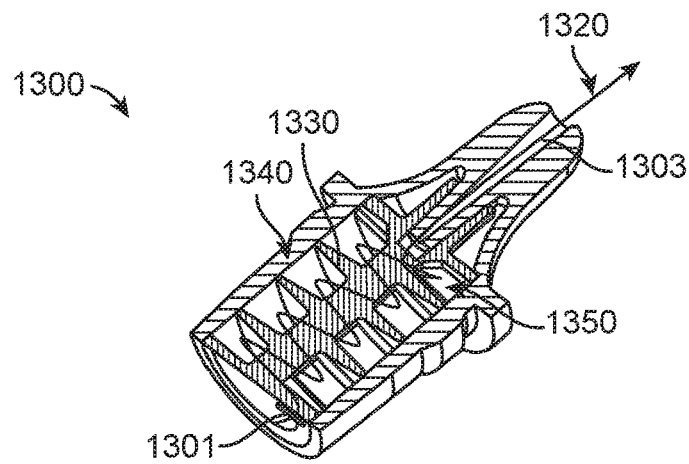
FIG. 13 illustrates a slice through a flow diverter with a "spiral" geometry integrated into a nozzle, in accordance with some embodiments.

FIG. 13 illustrates a slice through a flow diverter comprising a "spiral" geometry integrated into a nozzle, in accordance with some embodiments. Spiral geometry 1300 may comprise a flow path 1320, which may proceed from a fluid inlet 1301 to a fluid outlet 1303. A nozzle may comprise nozzle housing 1340 and flow diverter 1330. Geometry 1300 may be integrated into a nozzle using nozzle systems 300, 400, and 500 described herein. A nozzle may comprise a matrix 1350 disposed therein. Flow path 1320 may spiral from an inlet end to an outlet end of the nozzle radially around a central axis. In the illustrated embodiment, flow path 1320 comprises four full rotations around the axis of the nozzle. In some embodiments, flow path 1320 may comprise 1, 2, 5, 10, 20, 50, 100, 200, 500, 1000 rotations, or a number of rotations defined by range between any two of the preceding values.

Figure 14:
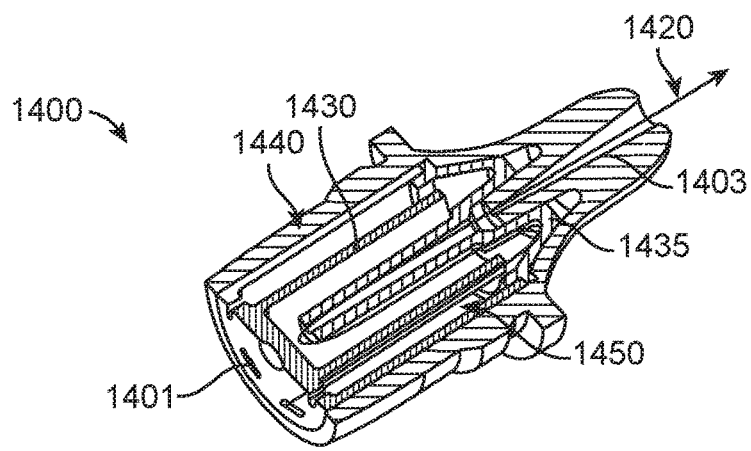
FIG. 14 illustrates a slice through a flow diverter with a "triple cuff" geometry integrated into a nozzle, in accordance with some embodiments.
Figure 15A:
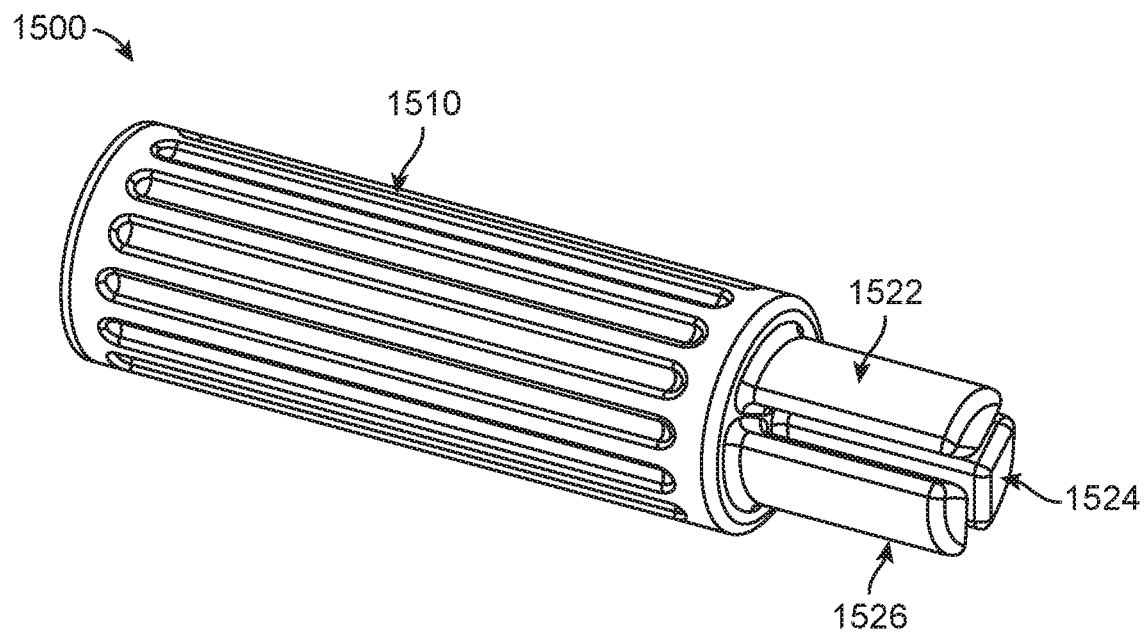
FIG. 15A illustrates an example compaction device for distributing a matrix within a nozzle comprising a dart geometry, in accordance with some embodiments
Figure 15B:
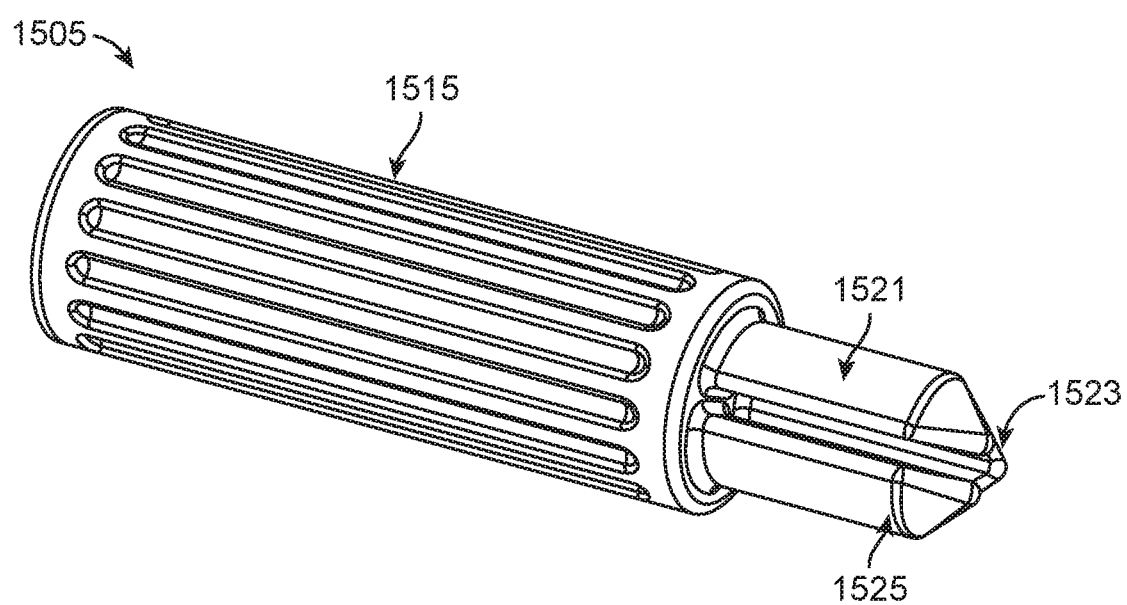
FIG. 15B illustrates an example compaction device comprising distal points for distributing a matrix within a nozzle comprising a dart geometry, in accordance with some embodiments.
Figure 16:
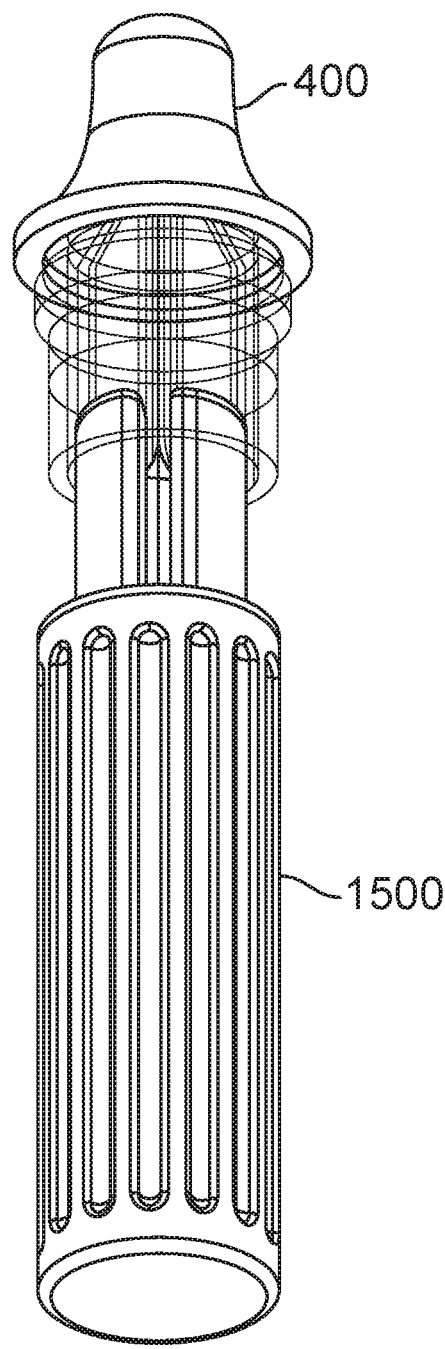
FIG. 16 illustrates a compaction device disposed within a nozzle system, in accordance with some embodiments
Figure 17:
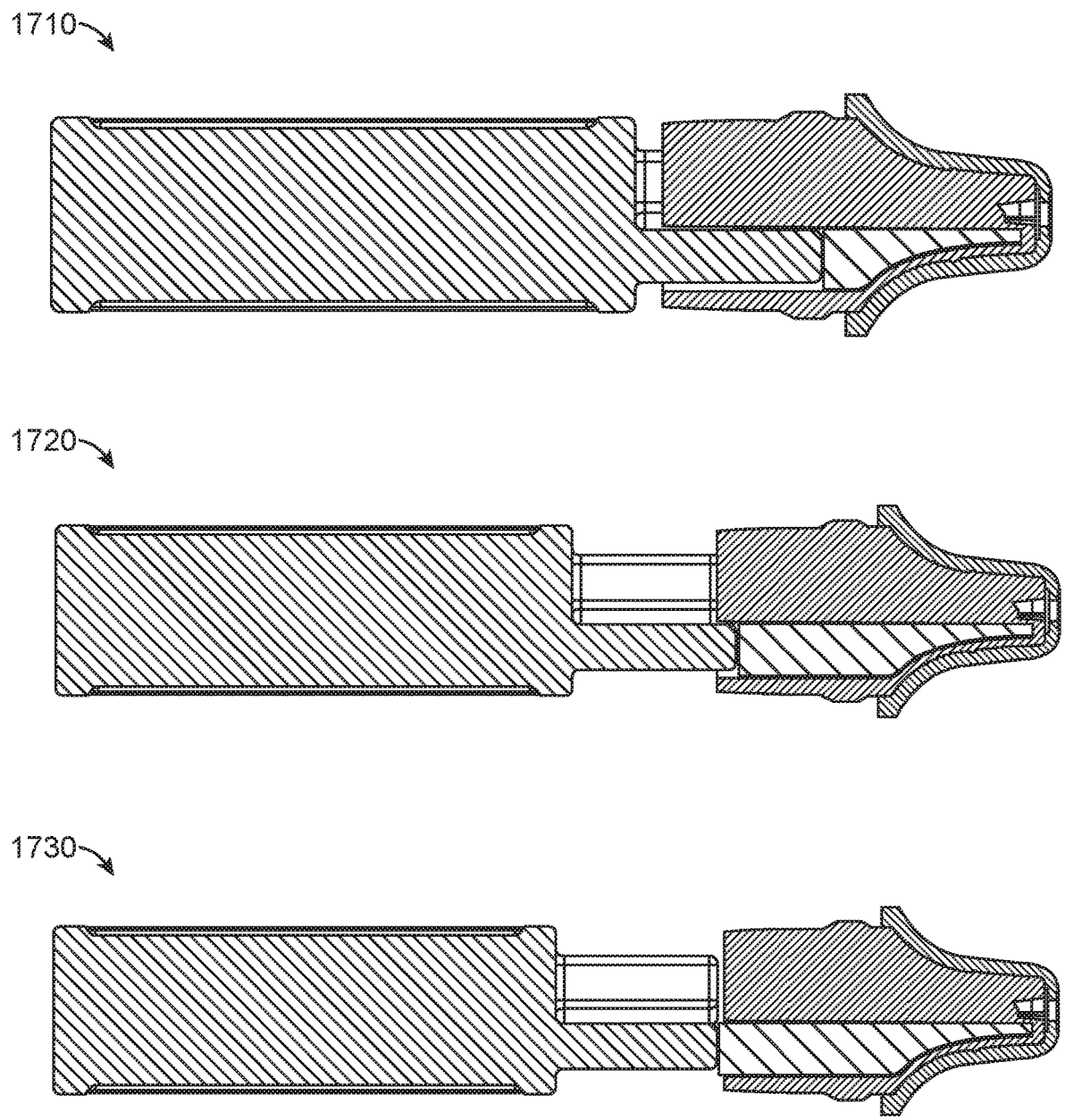
FIG. 17 illustrates an example method for distributing a matrix within a nozzle, in accordance with some embodiments.

FIG. 14 illustrates a slice through a flow diverter with a "triple cuff" geometry 1400 integrated into a nozzle, in accordance with some embodiments. Triple cuff geometry 1400 may comprise a flow path 1420, which may proceed from one or a plurality of fluid inlets 1401 to a fluid outlet 1403. A nozzle may comprise nozzle housing 1440 and two part flow diverter 1430 and 1435. Geometry 1400 may be integrated into a nozzle using nozzle systems 300, 400, and 500 described herein. A nozzle may comprise a matrix 1450 disposed therein. Flow path 1420 may proceed from the inlet side of the nozzle, through one or a plurality of fluid inlets 1401 radially arranged on an outer annular "cuff", toward the outlet side of the nozzle. Then the flow path may fold back toward the interior of the nozzle and proceed toward the inlet side of the nozzle, such that the second region of the flow path may comprise a second annular "cuff" with a smaller diameter than the first. Subsequently, the flow path may fold back again toward the interior of the nozzle and proceed toward the outlet side of the nozzle, such that the third region of the flow path may comprise a third annular "cuff" with a smaller diameter than the second "cuff". In the illustrated embodiment, flow path 1420 comprises three annular regions. In some embodiments, flow path 1420 may comprise 1, 3, 5, 11, 21, 51, 101, 201, 501, 1001 annular regions, or any odd number of annuli between a range defined my any two of the preceding values.

Embodiments of the present disclosure, which embodiments may comprise nozzles, nozzle systems, and flow diverter geometries, may comprise a matrix material disposed therein. The matrix material may comprise embodiments, variations, and examples of the porous polymeric matrix described herein. The matrix material may interact with a fluid, which fluid may comprise a therapeutic agent to be delivered to a patient eye. In order to interact with a fluid in a standardized manner, it may be beneficial to distribute a matrix within a nozzle in a manner which may be repeatable. In some embodiments, a compaction device may be employed to distribute a matrix within a nozzle. Alternatively, a matrix may be disturbed without a compaction device.

FIG. 15A illustrates an example compaction device 1500 for distributing a matrix within a nozzle comprising a dart geometry, in accordance with some embodiments. Compaction device 1500 may comprise handle portion 1510. Handle portion may comprise ridges, which ridges may improving grasping of handle portion 1510. Handle portion 1510 may be configured to be held by a press. Additionally or alternatively, handle portion 1510 may be configured to be held by a user, such as an assembler. Compaction device 1500 may comprise protrusions 1522, 1524, and 1526, which may be configured to fit within a nozzle comprising a dart geometry. Protrusions 1522, 1524, and 1526 may be flat topped. Compaction device 1500 may be used in conjunction with compaction device 1505. Alternatively, compaction device 1500 may be used with another variation or embodiment of a compaction device; however, compaction device 1500 may be used alone.

FIG. 15B illustrates an example compaction device 1505 comprising distal points for distributing a matrix within a nozzle comprising a dart geometry, in accordance with some embodiments. Compaction device 1505 may comprise handle portion 1515. Handle portion may comprise ridges, which ridges may improving grasping of handle portion 1515. Handle portion 1515 may be configured to be held by a press. Additionally or alternatively, handle portion 1515 may be configured to be held by a user, such as an assembler. Compaction device 1505 may comprise protrusions 1521, 1523, and 1525, which may be configured to fit within a nozzle comprising a dart geometry. Protrusions 1521, 1523, and 1525 may be pointed at the distal ends. Distal points of the protrusions may aid in compaction of a polymer near the tip of the nozzle. Compaction device 1505 may be used in conjunction with compaction device 1500. Alternatively, compaction device 1505 may be used with another variation or embodiment of a compaction device; however, compaction device 1505 may be used alone.

FIG. 16 illustrates compaction device 1500 disposed within nozzle system 400, in accordance with some embodiments. In the illustrated embodiment, compaction device 1500 fits within nozzle system 400 such that a matrix material may not ordinarily pass between the compaction device and the walls of the nozzle system. Compaction device 1500 may slide freely on the longitudinal axis of the nozzle system. Compaction device 1500 may slide under the force of a press or a user. While the illustrated embodiment shows compaction device 1500 disposed within nozzle system 400, similar compaction devices may be compatible with other flow diverter geometries and nozzle systems, such as, for example, flow diverter geometries and nozzle systems of the present disclosure. For example, a compaction device with a spiral shaped protrusion may be used with a nautilus geometry flow diverter. A compaction device with two concentric circular protrusions may be used with a concentric geometry flow diverter.

FIG. 17 illustrates an example method for distributing a matrix within a nozzle, in accordance with some embodiments. At a step 1710 of a method 1700, a first volume of a matrix material may be disposed within the nozzle. The first volume may be distributed within a nozzle by sliding a compaction device to compress a matrix material. At a step 1720 of a method 1700, a second volume of a matrix material may be disposed within the nozzle. The second volume may be distributed within a nozzle by sliding a compaction device to compress a matrix material. At a step 1730 of a method 1700, a final volume of a matrix material may be disposed within the nozzle. The final volume may be distributed within a nozzle by sliding a compaction device to compress a matrix material. A method 1700 may comprise any number of compaction steps, for example, a method 1700 may comprise 3, 5, 10, 20, 50, 100, 200, 500, or 1000 compaction steps; additionally or alternatively, a method 1700 may comprise a number of compaction steps within a range defined by any two of the preceding values. A volume of a matrix material to be added may be the same at every step of the method 1700; alternatively, a volume of a matrix material to be added may be different at every step of the method 1700. For example, the volume of a matrix material to be added may increase or may decrease. In some embodiments, the matrix material may be added continuously. A volume of a matrix material may comprise 100 mg of material. Additionally or alternatively, a volume of a matrix material may comprise 1, 2, 5, 10, 20, 50, 100, 200, 500, or 1000 mg of a matrix material; additionally or alternatively, a volume of a matrix material may comprise a quantity of material within a range defined may any two of the preceding values. In some embodiments, a method 1700 may additionally comprise leveling off the matrix material and/or sealing a bottle comprising a therapeutic agent.

Embodiments of the present disclosure provide a method for removing preservative from a therapeutic agent. The method may comprise receiving a solution comprising the therapeutic agent and a preservative. The solution may comprise a fluid comprising a therapeutic agent disclosed herein. Additionally, the solution may comprise a fluid comprising a preservative disclosed herein. The method may comprise squeezing a compressible bottle comprising a nozzle for delivery of the therapeutic agent to an eye. The nozzle may comprise an embodiment, variation, or example of the nozzles and nozzle systems disclosed herein. The squeezable bottle may comprise a standard bottle, a commercially available bottle, or another embodiment of a squeezable bottle disclosed herein. In some embodiments, the nozzle comprises a fluid inlet, a fluid outlet, and a flow path extending from the fluid inlet to the fluid outlet as described with respect to FIG. 2 and embodiments, examples, and variations of nozzle systems 300, 400, and 500 herein. In some embodiments, the flow diverter directs flow of the solution in a plurality of different directions, the flow path greater than the distance from the inlet to the outlet. The flow diverter may comprise the flow diverter of nozzle geometries of FIG. 3A to FIG. 14. Devices with Non-inert Filters In some embodiments, a device may comprise several types of filter including a screen, an inert material, and a filter material which may not be inert to remove one or more components of preservatives from formulations as described elsewhere herein, such as the preservatives described herein. For example, one or more multi-dosing devices described herein can comprise a non-inert filter which removes for removal of the zinc-containing components and/or chlorine-containing components from the preservatives. In some embodiments, the filter can be configured to provide desired removal of zinc-containing components and/or chlorine-containing components in preservatives in delivered eye drops while retaining the zinc-containing components and/or chlorine-containing components in the contained formulation to ensure that the eye drop bottle remains sterile.

Preservatives which comprise zinc-containing preservatives may include, for example, Sofzia® (e.g., commercially available from Alcon, Inc., USA). Sofzia® can comprise zinc, borate, propylene glycol and glycerine. One or more filters described herein can be configured to selectively remove the zinc from the Sofzia® composition as the eye drop solution is passed through the filter. Benefit of the zinc-containing preservative for storage may be retained while reducing or eliminating adverse effects the zinc-containing component may have on a patient, including any risk for ocular toxicity.

Preservatives comprising chlorine-containing components, such as sodium hypochlorite, can include Purite® (e.g., commercially available from Allergan, Inc., USA). One or more filters described herein may be configured to selectively remove chlorine-containing components from the Purite® composition as the eye drop solution is passed through the filter to reduce adverse effects the chlorine-containing components can have on a patient's eye.

In some embodiments, the filter comprises a zinc-removal agent comprising desired affinity for the zinc-containing component of the preservative such that a desired quantity of the zinc-containing component can be removed from the eye drop solution as the solution passes over the material in the preservative removing device. The zinc-removal agent can be configured to have selective affinity for the zinc-containing component. In some embodiments, the zinc-removal agent comprises a metal chelating agent. In some embodiments, the zinc-removal agent comprises ethylenediaminetetraacetic acid (EDTA). In some embodiments, the zinc-removal agent comprises a salt of EDTA, such as edetate calcium disodium.

Figure 19:
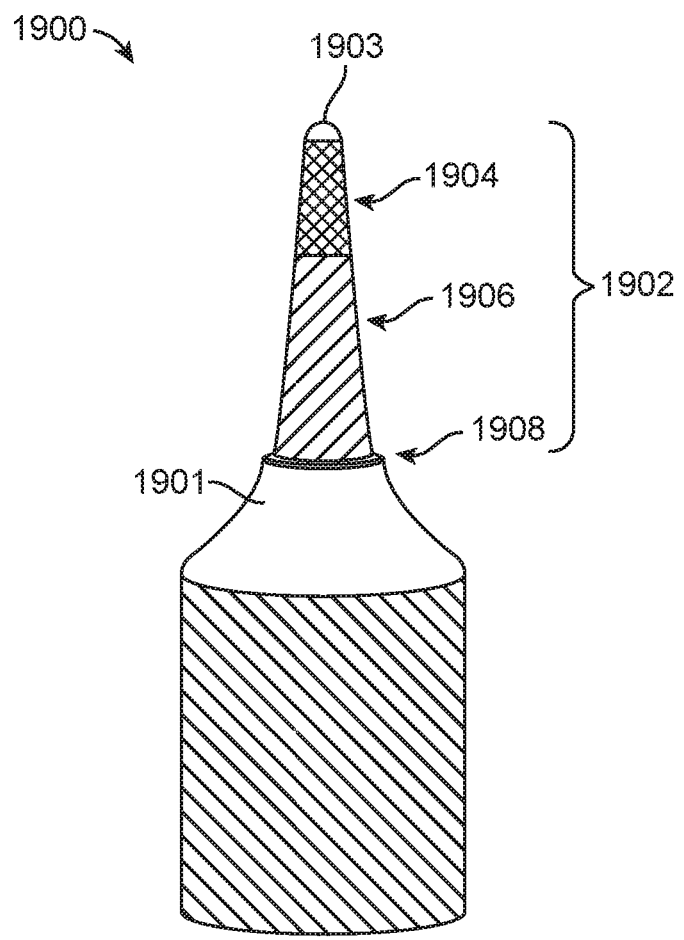
FIG. 19 is a schematic diagram of an eye drop bottle in accordance with some embodiments.

In an embodiment, a porous filter is situated in the dispensing pathway of an eye drop bottle, such as in the nozzle of the eye drop bottle leading to the drop exit. An example of an eye drop bottle 1900 comprising a filter 1902 as shown in FIG. 19. The bottle 1900 can comprise a nozzle comprising a first end having an opening through which the eye drop solution is dispensed from the bottle to the patient, and an opposing second end. The nozzle can be detachable from the bottle 1900 and/or integrally formed with the bottle. The filter 1902 can be positioned within the nozzle. Referring to FIG. 19, in some embodiments, the filter 1902 can comprise one or more of a chlorine-removal agent, a zinc-removal agent, an inert material, and a screen. At least a portion of the chlorine-removal agent and/or the zinc-removal agent can be positioned at or proximate to the opening in the nozzle of the bottle. The chlorine-removal agent and/or the zinc-removal agent can be separated from the eye drop solution in the bottle by the inert material and the screen. The screen can be configured to be positioned proximate to or adjacent to the second end of the nozzle such that the inert material is positioned between the screen and the chlorine-removal agent and/or the zinc-removal agent. The inert material and/or the screen can facilitate maintaining a separation distance between eye drop solution within the bottle and the zinc-removal agent and/or chlorine-removal agent. In some embodiments, the inert material and/or the screen can be configured to maintain desired positioning of the zinc-removal agent and/or chlorine-removal agent within the nozzle, such as proximate or adjacent to the opening of the nozzle. The inert material may serve as packing material. In some embodiments, the screen can be configured to maintain a fixed position within the nozzle so as to facilitate maintaining the position of the inert material and the zinc-removal agent and/or chlorine-removal agent within the nozzle. Eye drop solution passes through the screen to the inert material and then through the zinc-removal agent and/or chlorine-removal agent, and then out through the opening of the nozzle to the patient.

The bottle 1900 can comprise EDTA positioned proximate or adjacent to the opening at the first end the nozzle. For example, the EDTA can be packed within at least a portion of the nozzle such that at least a portion of the EDTA is positioned proximate or adjacent to the opening. In some embodiments, the EDTA can be included in the nozzle as a salt, such as in crystalline form. In some embodiments, the EDTA can be dissolved and coated onto an inert material and the EDTA coated inert material can be packed within the nozzle. The inert material can comprise a composition as described herein. For example, the inert material can comprise a plurality of beads, including polystyrene beads, such that the dissolved EDTA can be used to coat the polystyrene beads. The EDTA can be positioned adjacent to an inert material, which is positioned adjacent to a screen. The screen can be positioned proximate to or adjacent to the second end of the nozzle. In some embodiments, the bottle 1900 can include activated charcoal positioned proximate or adjacent to the opening at the first end the nozzle. The activated charcoal can be packed within at least a portion of the nozzle such that at least a portion of the activated charcoal is positioned proximate or adjacent to the opening of the nozzle. The activated charcoal can be positioned adjacent to an inert material, which can be positioned adjacent to a screen. The screen can be positioned proximate to or adjacent to the second end of the nozzle.

In some embodiments, the zinc-removal agent and/or chlorine-removal agent (e.g., EDTA and/or activated charcoal) can be packed in about the top ⅓ of the nozzle. In some embodiments, the zinc-removal agent and/or chlorine-removal agent (e.g., EDTA and/or activated charcoal) can be in particle form, ranging from particles having a longest dimension, such as diameter of about 10 microns to about 1 mm.

The inert material may comprise a polymeric material. In some embodiments, the inert material can comprise cellulose, such as cellulose fibers. In some embodiments, the inert material comprises polymeric beads, such as polystyrene beads. The inert material can have configured to allow the eye drop solution to flow through the EDTA and/or charcoal in a controlled manner in order to ensure sufficient contact time between ingredients of the solution and the EDTA and/or charcoal.

The screen may comprise a polymeric material, such as a plastic material, comprising plurality of openings to allow the eye drop solution to flow therethrough into the nozzle. The mesh screen may comprise a plurality of inlet apertures, which apertures may comprise on or a plurality of fluid inlets.

In some cases, an inert material and at least one of a chlorine-removal agent and a zinc-removal agent may be placed adjacent other bottle geometries comprising meshes or screens of the present disclosure. For example, filter system 1902 may be integrated in the place of a screen in nozzle system 300, nozzle system 400, nozzle system 500, each of which may comprise examples, variations, and embodiments of flow diverter geometries shown in FIG. 6A, FIG. 6B, FIG. 7A, FIG. 7B, FIG. 8A, FIG. 8B, FIG. 9, FIG. 10, FIG. 11, FIG. 12, FIG. 13, and FIG. 14.

In some examples, filter system 1902 may be disposed at a fluid inlet. In some examples filter system 1902 may be disposed at a fluid outlet. The filter system 1902 may comprise an example of an inlet cap. The filter system 1902 may comprise an example of an outlet cap. The filter system 1902 may aid in retaining a matrix material within the nozzle system. The filter system 1902 may be used in place of a matrix material.

An eye drop bottle configured to receive an eye drop solution can comprise the filter as described herein. In some cases, a filter may remove a desired quantity of the zinc-containing components and/or chlorine-containing components from the solution as the solution passes through the filter, while facilitating retaining sufficient preservative activity in the eye drop solution retained within the bottle. For example, the filter can be configured to facilitate removal of a desired quantity of the zinc-containing component and/or chlorine-containing component from the eye drop solution dispensed from the bottle while allowing sufficient zinc-containing components and/or chlorine-containing components to be retained in the eye drop solution retained within the bottle such that the solution retained in the bottle remains sterile.

Preservative Removal Agent

The present disclosure provides a preservative removal agent. A preservative removal agent may rapidly and selectively remove preservatives of the present disclosure from a solution, emulsion, or suspension comprising a therapeutic agent. The preservative removal agent may rapidly and selectively extract the preservative, allowing the eye drop formulation to flow through the plug with minimal pressure drop, yet with sufficient time to remove the preservative and with sufficient surface area to adsorb the preservative. The matrix may comprise a material with a high affinity for the preservative, such as for example benzalkonium chloride (BAK), and low affinity for a drug or other ophthalmological agent. The preservative removal agent may be sufficiently selective, such that at least 50 percent of the preservative may be removed and at least 50 percent of the drug may be retained by the solution.

In some embodiments, a matrix disposed within a nozzle may be a porous polymeric matrix. The porous polymeric matrix may comprise a variety of materials. Such material may be safe and biocompatible. Such material may comprise but is not limited to, for example, Poly(2-hydroxyethyl methacrylate) (pHEMA), poly(hydroxylethyl methacrylate-co-methacrylic acid), dimethyl acrylamide, methyl methacrylate, silicones, and/or any combination of the preceding materials.

In some embodiments, the porous polymeric matrix may comprise one or more hydrophilic monomer. In some examples, hydrophilic monomers may be acrylic- or vinyl-containing. In some examples, a hydrophilic monomers may itself be used as crosslinking agents. Hydrophilic vinyl-containing monomers which may be incorporated into the porous polymeric matrix include monomers such as N-vinyl lactams (e.g. N-vinyl pyrrolidone (NVP)), N-vinyl-N-methyl acetamide, N-vinyl-N-ethyl acetamide, N-vinyl-N-ethyl formamide, N-vinyl formamide, etc. Hydrophilic acrylic-containing monomers which may be incorporated into the porous polymeric matrix include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, etc. Hydrophilic monomers may comprise vinyl carbonate and vinyl carbamate monomers.

In some embodiments, a porous polymeric matrix comprises at least one hydrophobic monomer. A hydrophobic monomer may include but is not limited to methacryloxypropyltris(trimethylsiloxy)silane (TRIS), monomethacryloxypropyl terminated polydimethylsiloxane (mPDMS), t-butyl methacrylate (TBM), and silicone macromers.

Polymeric matrices of the present disclosure may comprise a hydrophilic monomer and a hydrophobic monomer. In some examples, polymeric matrices of the present disclosure may comprise two more of any of the hydrophilic or hydrophobic monomers disclosed herein. In some examples, the porous polymeric matrix comprises 5% to 25% HEMA and the 75% to 95% TBM. In some examples, the porous polymeric matrix comprises 5% to 25% MAA and 75% to 95% TBM.

In some embodiments, the porous polymeric matrix may comprise a cross linker. Examples of crosslinking agents include: polyvinyl, typically di- or tri-vinyl monomers, the di- or tri(meth)acrylates of dihydric ethylene glycol, triethylene glycol, butylene glycol, hexane 1,6-diol, thio-diethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentanerythritol, butylene glycol, manitol, and sorbitol.

In some embodiments, the matrix may be highly porous. The pore size in the matrix may be small enough so that the molecules, which may initially be far from the surface of the polymer in the matrix, may diffuse towards the polymer and adsorb. A matrix may have large interconnected pores which may allow flow of solution and adsorption of the preservative into the pores. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix is a hydrogel. In some embodiments, the matrix may comprise a packed bed of pHEMA or other polymeric particles. The particles may be macroporous. The particles may be spherical or non-spherical. In some embodiments, the polymeric matrix may comprise nano or micron sized polymeric particles (e.g., nanogels or microgels). In some embodiments, the polymeric matrix may comprise a cryogel. In some embodiments, the particles themselves may directly impart the preservative effect, such as colloidal silver nanoparticles.

In certain embodiments, particles of the formulations described herein have an average diameter from about 1 nm to about 10 μm, about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, greater than 80% of the particles, such as greater than 90% or greater than 95% of the particles in the formulation have an average largest particle diameter of from about 1 nm to about 10 μm, about 1 nm to about 10 μm, about 1 nm to about 5 μm, about 1 nm to about 2 μm, about 1 nm to about 1 μm, about 1 nm to about 900 nm, about 1 nm to about 800 nm, about 1 nm to about 700, about 1 nm to about 600 nm, about 1 nm to about 500 nm, about 1 nm to about 400 nm, about 1 nm to about 300 nm, about 1 nm to about 200 nm, or even from about 1 nm to about 100 nm. In certain embodiments, the average diameter is the average largest diameter or the average equivalent diameter.

In certain embodiments, particles of the formulations described herein have an average diameter from about 100 nm to about 10 μm, about 100 nm to about 10 μm, about 100 nm to about 5 μm, about 100 nm to about 2 μm, about 100 nm to about 1 μm, about 100 nm to about 900 nm, about 100 nm to about 800 nm, about 100 nm to about 700 nm, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter.

In certain embodiments, greater than 80% of the particles, such as greater than 90% or greater than 95% of the particles in the formulation have an average diameter from about 100 nm to about 10 μm, about 100 nm to about 10 μm, about 100 nm to about 5 μm, about 100 nm to about 2 μm, about 100 nm to about 1 μm, about 100 nm to about 900 nm, about 100 nm to about 800 nm, about 100 nm to about 700 nm, about 100 nm to about 600 nm, about 200 nm to about 500 nm, about 250 nm to about 600 nm, about 300 nm to about 600 nm, about 350 nm to about 700 nm, about 450 nm to about 550 nm, about 475 nm to about 525 nm, or from about 400 nm to about 700 nm. In certain embodiments, the average diameter is the average largest diameter or the average equivalent diameter The matrix may comprise a tortuosity such that the flow path of a solution, emulsion, or suspension through the nozzle may be significantly increased. In an embodiment where the matrix is a packed bed of macroporous particles, the packed beds of macroporous particles may have three levels of porosity: the space between the particles, the macropores in the particles, and the inherent porosity of the polymer. In such an embodiment, all three levels of porosity may contribute to the tortuosity of the matrix.

In some embodiments, a matrix disposed within a nozzle may be a porous polymeric matrix. Applying a pressure behind the nozzle may cause fluid to flow through the nozzle via the flow path, along which path the preservative may be removed by adsorption onto the matrix. The polymer material, the hydraulic permeability, the partition coefficient, the adsorption rate, and the pore size in combination may aid in the absorption of all or most of the preservative from the solution and thus patient eye drops. The reduced preservative solution may subsequently be delivered directly to the eye. The porous polymeric matrix may rapidly and selectively extract the preservative, allowing the eye drop formulation to flow through the plug with minimal pressure drop, yet with sufficient time to remove the preservative and with sufficient surface area to adsorb the preservative.

The porous polymeric matrix may comprise a variety of materials. Such material may be safe and biocompatible. Such material may comprise but is not limited to, for example, Poly(2-hydroxyethyl methacrylate) (pHEMA), poly(hydroxylethyl methacrylate-co-methacrylic acid), dimethyl acrylamide, methyl methacrylate, silicones, and/or any combination of the preceding materials. The matrix may comprise a material with a high affinity for the preservative, such as for example benzalkonium chloride (BAK), and low affinity for a drug or other ophthalmological agent. The porous polymeric matrix may comprise a high affinity for the preservative, such that at least 50 percent of the preservative may be removed and at least 50 percent of the drug may be retained by the solution.

While example systems and methods of the present disclosure may be directed to pHEMA and BAK, any matrix material and any drug may be used such that the drug's partition coefficient into the matrix may be lower by at least an order of magnitude than the matrix's affinity for the preservative. For example, pHEMA may bind BAK with a partition coefficient of about 100-500 depending on the BAK concentration and the structure of the matrix. In some embodiments, the matrix may comprise a partition coefficient for the preservative from the solution, emulsion, or suspension of, for example, at least 10, at least 100, at least 1000, at least 10,000, or within a range defined by any two of the preceding values. Additionally or alternatively, the adsorption rate constant may be sufficiently high so that the time for adsorption of a drug molecule to the polymer may be less than the time to form a drop. The time to form a drop may comprise a time within a range from 0.1 to 10 seconds.

The matrix may display a high hydraulic permeability such that relatively little pressure may be required to dispense a fluid. The hydraulic permeability may depend on the design of the filter. Larger pores may allow for higher flow for a given pressure drop. In some embodiments, hydraulic permeability may be larger than about 0.01 Darcy. A nozzle may comprise a permeability of about 0.1 Darcy. A hydraulic permeability of 1 to 10 Darcy may allow fluid to be retained in the filter during instances when the pressure may be lowered subsequent to formation of a drop. A larger hydraulic permeability may allow the same plug to work for a wide range of formulations including, for example, high viscosity formulations, such as rewetting eye drops. In some embodiments, the porous polymeric matrix comprises a hydraulic permeability of, for example, 0.01 Da, 0.1 Da, 1 Da, 10 Da, 100 Da, 1000 Da or a hydraulic permeability within a range defined by any two of the preceding values.

In some embodiments, the matrix may be highly porous. The pore size in the matrix may be small enough so that the molecules, which may initially be far from the surface of the polymer in the matrix, may diffuse towards the polymer and adsorb. A matrix may comprise large interconnected pores which may allow flow of solution and adsorption of the preservative into the pores. The matrix may be formed as a porous gel, as a packed bed, and/or a structure formed by 3D printing soft lithography, electrospinning, or any other appropriate method. In some embodiments, the matrix may comprise a microporous gel. In some embodiments, the matrix may comprise a packed bed of pHEMA or other polymeric particles. The particles may be macroporous. The particles may be spherical or non-spherical. In some embodiments, the polymeric matrix may comprise nano or micron sized polymeric particles (e.g., nanogels or microgels). In some embodiments, the polymeric matrix may comprise a cryogel. In some embodiments, the particles themselves may directly impart the preservative effect, such as colloidal silver nanoparticles.

In some embodiments, the particles may need to be stably held in the nozzle and prevented from eluting from the nozzle. The particles may be attached to the container walls through long polymeric chains and/or by placing a filter at the exit from the device. Additionally or alternatively, the walls of the container or other surfaces may comprise preservative attached thereupon and/or incorporated therein. In such embodiments, the preservative source comprises a pHEMA membrane with 1-10% by volume equilibrated with BAK. In some embodiments, the matrix comprises pre-loaded with BAK at a concentration to inhibit microbial growth over time.

Alternatively or in combination with the flow diverter as described herein, the porous matrix material may comprise a tortuosity such that the flow path of a solution, emulsion, or suspension through the nozzle increases. In some embodiments where the matrix comprises a packed bed of macroporous particles, the packed beds of macroporous particles may comprise three levels of porosity: the space between the particles, the macropores in the particles, and the inherent porosity of the polymer. In such embodiments, all three levels of porosity may contribute to the tortuosity of the matrix. The tortuosity of the porous material combined with the flow diverter may increase the flow path in accordance with a multiplicative factor of a first flow path length corresponding to flow defined by the flow diverter and a second flow path length corresponding to the tortuosity of the porous material.

The tortuosity of the matrix may increase the flow path by a multiplicative factor. In an example, if the flow path through the nozzle increases by a factor of 1.5 by a flow diverter within the nozzle, the tortuosity increases the flow path a multiplicative factor of, for example, 1.5 such that the total flow path increases by the multiplicative factor of 2.25, for example. In another example, if the flow path through the nozzle increases by a factor of 2.0 by a flow diverter within the nozzle, the tortuosity increases the flow path a multiplicative factor of, for example, 1.5 such that the total flow path increases 3.0. In some embodiments, the flow path comprises a factor such as a multiplicative factor within a range from 1.5 to any of the prior values, e.g. from 1.5 to 2.25.

In an example, if the flow path through the nozzle increases by a factor of 3.5 by a flow diverter within the nozzle, the tortuosity may increase the flow path a multiplicative factor of, for example, 1.5 such that the total flow path may be increased by up to 3.75 but at least 1.5. In an alternative example, if the flow path through the nozzle increases by a factor of 3 by a flow diverter within the nozzle, the tortuosity may increase the flow path a multiplicative factor of, for example, 1.5 such that the total flow path may increase by up to 4.5 but at least 1.5. In an alternative example, if the flow path through the nozzle increases by a factor of 5 by a flow diverter within the nozzle, the tortuosity may increase the flow path a multiplicative factor of, for example, 1.5 such that the total flow path may be increased by up to 7.5 but at least 1.5.

In an example, if the flow path through the nozzle increases by a factor of 1.5 by a flow diverter within the nozzle, the tortuosity increases the flow path a multiplicative factor of, for example, 2.0 such that the total flow path increases by the multiplicative factor of 2.25, for example. In another example, if the flow path through the nozzle increases by a factor of 2.0 by a flow diverter within the nozzle, the tortuosity increases the flow path a multiplicative factor of, for example, 2.0 such that the total flow path increases 3.0. In some embodiments, the flow path comprises a factor such as a multiplicative factor within a range from 2.0 to any of the prior values, e.g. from 2.0 to 2.5.

In an alternative example, if the flow path through the nozzle increases by a factor of 3.5 by a flow diverter within the nozzle, the tortuosity may increase the flow path a multiplicative factor of, for example, 2.0 such that the total flow path may be increased by up to 3.75 but at least 2.0. In an alternative example, if the flow path through the nozzle increases by a factor of 3 by a flow diverter within the nozzle, the tortuosity may increase the flow path a multiplicative factor of, for example, 2.0 such that the total flow path may increase by up to 4.5 but at least 2.0. In an alternative example, if the flow path through the nozzle increases by a factor of 5 by a flow diverter within the nozzle, the tortuosity may increase the flow path a multiplicative factor of, for example, 2.0 such that the total flow path may be increased by up to 7.5 but at least 2.0.

In an example, if the flow path through the nozzle increases by a factor of 1.5 by a flow diverter within the nozzle, the tortuosity increases the flow path a multiplicative factor of, for example, 3.0 such that the total flow path increases by the multiplicative factor of 2.25, for example. In another example, if the flow path through the nozzle increases by a factor of 3.0 by a flow diverter within the nozzle, the tortuosity increases the flow path a multiplicative factor of, for example, 3.0 such that the total flow path increases 3.0. In some embodiments, the flow path comprises a factor such as a multiplicative factor within a range from 3.0 to any of the prior values, e.g. from 3.0 to 3.5.

In an alternative example, if the flow path through the nozzle increases by a factor of 3.5 by a flow diverter within the nozzle, the tortuosity may increase the flow path a multiplicative factor of, for example, 3.0 such that the total flow path may be increased by up to 3.75 but at least 3.0. In an alternative example, if the flow path through the nozzle increases by a factor of 3 by a flow diverter within the nozzle, the tortuosity may increase the flow path a multiplicative factor of, for example, 3.0 such that the total flow path may increase by up to 4.5 but at least 3.0. In an alternative example, if the flow path through the nozzle increases by a factor of 5 by a flow diverter within the nozzle, the tortuosity may increase the flow path a multiplicative factor of, for example, 3.0 such that the total flow path may be increased by up to 7.5 but at least 3.0.

The pressure needed for drop creation may exceed the Young Laplace pressure during drop creation, which may be about $2\sigma/R_d$ where G is the surface tension and $R_d$ is the radius of the drop. Estimating $R_d$~0.5 mm based on a drop volume of 30 µL, and using the surface tension of water may yield a Young Laplace pressure of about 100 Pa. The pressure to form a drop may additionally exceed the pressure needed to displace 30 µL of volume. Typical drop volumes may comprise a volume within a range between 1 µL and 100 µL. The minimum pressure to form a drop may be 0.01 Atm (1000 Pa) based on an ideal gas estimate using a 3 mL bottle at atmospheric pressure, but may be lower for larger bottles at varying pressures. Maximum pressure to form a drop may be limited by a patient strength. The pressure to form a drop may be within a range between 0.01 Atm and 0.5 Atm.

The rate of liquid flow through the plug may depend on the applied pressure as well as the design parameters of the matrix including, but not limited to, length, area, porosity, hydraulic permeability, flow path length, etc. These design parameters may be considered individually or in combination to remove preservative without excessive squeeze pressure. The rate of liquid flow may affect the time to form a drop.

Formulation Comprising a Therapeutic Agent

Embodiments of the present disclosure may provide a therapeutic agent for delivery to an eye. A therapeutic agent may be integrated into a fluid, which may flow from a container to an eye through a nozzle. In some embodiments, the fluid may comprise a solution, emulsion, or suspension comprising a therapeutic agent. The solution, emulsion, or suspension may comprise a therapeutic agent. Example therapeutic agents which may be used in conjunction with a nozzle include but are not limited to: timolol, dorzolamide, dexamethoasone phosphate, dexamethasone, Betimol, olopatadine, brimonidine, trahydrozoline, latanoprostene bunod, latanoprost, and combinations of any two or more thereof. Therapeutic agents may comprise brand name drugs and formulations including, but not limited to, Timoptic, Xalatan, Combingan, Lumigan, Pataday, Pazeo, Trusopt, Cosopt, Alphagan, Visine, Vyzulta, Veseneo, and other agents described herein such as in the following tables. The therapeutic agents may be dissolved in aqueous solution. The solution may be sterilized and buffered to appropriate pH. In some embodiments, the solution may comprise inactive ingredients such as sodium chloride, sodium citrate, hydroxyethyl cellulose, sodium phosphate, citric acid, sodium dihydrogen phosphate, polyoxyl 40 hydrogenated castor oil, tromethamine, boric acid, mannitol, edetate disodium, sodium hydrdroxide, and/or hydrochloric acid. In some embodiments, the fluid comprises a preservative in addition to a therapeutic agent. Example preservatives include but are not limited to: benzalkonium chloride (BAK), alcohols, parabens, methyl paraben, polyparben, EDTA, chlorhexidine, quaternary ammonium compounds, Purite®, stabilized oxychloro complexes, Sofzia®, sorbic acid, Sodium perborate, polyquaternium-1, chlorobutanol, cetrimonium chloride, edatate disodium, etc.

Therapeutic agents for the treatment of for example, dry eye, bacterial infection, glaucoma, hypertension, inflammation, allergic conjunctivitis, hypotrichosis of the eyelashes, fungal infection, etc. and therapeutic agents used for local anesthetic, pupil dilation, etc. may be administered to a patient as a solution, emulsion, or suspension delivered to an eye topically via a dropper bottle or similar delivery mechanism. The solution, emulsion, or suspension may be subject to contamination such as microbial, fungal, or particulate contamination, which may be adverse to patient health. In order to prevent such contamination a preservative may be added to the solution, emulsion, or suspension; however, patient exposure to preservatives may have adverse effects to eye health. It may be advantageous to limit patient exposure to preservative by adding an additional element to a pharmaceutical formulation which may remove a preservative from the solution, emulsion, or suspension.

Non-limiting examples of a preservative removal agents may comprise solid, gel, and/or particulate matrices. The preservative removal agent may act as a physical barrier or filter. Additionally or alternatively, the preservative removal agent may chemically remove a preservative such as by adsorption of the preservative onto the matrix. The preservative removal agent may be disposed in the outlet of a container, which container may contain the solution, emulsion, or suspension.

In some embodiments, the disclosure provides pharmaceutical formulations of a preservative, a preservative removal agent, and a therapeutic agent. The formulation may comprise a solution, emulsion, or suspension of a therapeutic agent and a preservative. In some embodiments, the formulation may comprise a preservative removal agent, (e.g. in embodiments where the preservative removal agent may comprise a portion of a solution, emulsion, or suspension comprising a therapeutic agent and a preservative). In other embodiments, the preservative removal agent may be separate from the solution, emulsion, or suspension comprising the therapeutic agent and the preservative (e.g. in embodiments where the preservative removal agent may be located within the neck of a bottle). Optionally in any embodiment, the solution, emulsion, or suspension may additionally comprise one or more pharmaceutically acceptable excipients.

Compounds of the Disclosure

The present disclosure provides pharmaceutical formulations which may comprise a solution, emulsion, or suspension of a therapeutic agent and a preservative. The therapeutic agent may comprise one or more ophthalmic agents. Therapeutic agents may comprise compounds and salts, for use in the treatment of ophthalmic diseases. The disclosed compounds and salts can be used, for example, for the treatment or prevention of vision disorders and/or for use during ophthalmological procedures for the prevention and/or treatment of ophthalmic disorders. The flowing list of examples are not intended to be limiting.

In some embodiments, the therapeutic agent to be dispensed comprises an active ingredient selected from cyclosporine and lifitegrast. In such embodiments, the therapeutic agent may be an active ingredient in the treatment of dry eye.

In some embodiments, the therapeutic agent to be dispensed comprises an active ingredient selected from sulfacetamide sodium, ofloxacin, gatifloxacin, ciprofloxacin, moxifloxacin, tobramycin, levofloxacin, prednisolone acetate, polymyxin B sulfate, and trimethoprim. In some embodiments, the therapeutic formulation to be dispensed comprises the active ingredients sulfacetamide sodium and prednisolone acetate. In some embodiments, the therapeutic formulation to be dispensed comprises the active ingredients polymyxin B sulfate and trimethoprim. In such embodiments, the therapeutic agent may be an active ingredient in the treatment of a bacterial infection.

In some embodiments, the therapeutic agent to be dispensed comprises an active ingredient selected from brimonidine tartrate, bimatroprost, levobunolol hydrochloride, brinzolamide, betaxolol hydrochloride, pilocarpine hydrochloride, apraclonidine, travoprost, timolol maleate, latanoprost, dorzolamide hydrochloride, timolol maleate, and tafluprost. In some embodiments, the therapeutic formulation to be dispensed comprises the active ingredients brimonidine tartrate and timolol maleate. In some embodiments, the therapeutic formulation to be dispensed comprises the active ingredients brinzolamide and brimonidine tartrate. In such embodiments, the therapeutic agent may be an active ingredient in the treatment of glaucoma or hypertension.

In some embodiments, the therapeutic agent to be dispensed comprises an active ingredient selected from ketorolac tromethamine, fluorometholone, prednisolone acetate, difluprednate, fluorometholone acetate, nepafenac, dexamethasone, diclofenac sodium, bromfenac, gentamicin, tobramycin, neomycin, and polymyxin B sulfate. In some embodiments, the therapeutic formulation to be dispensed comprises the active ingredients gentamicin and prednisolone acetate. In some embodiments, the therapeutic formulation to be dispensed comprises the active ingredients tobramycin and dexamethasone. In some embodiments, the therapeutic formulation to be dispensed comprises the active ingredients neomycin, polymyxin B sulfate and dexamethasone. In such an embodiment, the therapeutic agent may be an active ingredient in the treatment of inflammation.

In some embodiments, the therapeutic agent to be dispensed comprises an active ingredient selected from nedocromil sodium, epinastine HCl, alcaftadine, lodoxamide tromethamine, emedastine difumarate, and olopatadine hydrochloride. In such embodiments, the therapeutic agent may be an active ingredient in the treatment of allergic conjunctivitis.

In some embodiments, the therapeutic agent to be dispensed comprises an active ingredient selected from proparacaine hydrochloride and tetracine hydrochloride. In such embodiments, the therapeutic agent may be a local anesthetic.

In some embodiments, the therapeutic agent to be dispensed comprises an active ingredient selected from cyclopentolate hydrochloride, atropine sulfate, and tropicamide. In some embodiments, the therapeutic formulation to be dispensed comprises the active ingredients cyclopentolate hydrochloride and phenylephrine hydrochloride. In such embodiments, the therapeutic agent may dilate pupils.

In some embodiments, the therapeutic agent to be dispensed comprises the active ingredient natamycin. In such embodiments, the therapeutic agent may be an active ingredient in the treatment of fungal infection.

In some embodiments, the therapeutic agent to be dispensed comprises an active ingredient selected from lipoic acid choline ester chloride, rebamipide, pilocarpine, ketorolac, aceclidine, tropicamide, sodium hyaluronate, diclofenac sodium, pilocarpine HCl, and ketorolac. In some embodiments, the therapeutic formulation to be dispensed comprises the active ingredients aceclidine and tropicamide. In some embodiments, the therapeutic formulation to be dispensed comprises the active ingredients sodium hyaluronate and diclofenac sodium and pilocarpine HCl. In some embodiments, the therapeutic formulation to be dispensed comprises the active ingredients pilocarpine and ketorolac. In such embodiments, the therapeutic agent may be an active ingredient in the treatment of presbyopia.

The present disclosure provides formulations comprising one or more preservatives for solutions, emulsions, or suspensions of therapeutic agents of the present disclosure. Preservatives may comprise compounds and salts, for use as preservatives for solutions, emulsions, or suspensions of therapeutic agents. The one or more preservatives may for example prevent microbial and/or fungal growth. The one or more preservatives may for example prevent physical or chemical deterioration of a therapeutic agent.

Non-limiting examples of preservative agents include benzalkonium chloride, ethylenediaminetetraacetic acid (EDTA), chlorbutanol, phenylmercuric acetate, phenylmercuric nitrate, chlorhexidine acetate, thimerosal, benzethonium chloride, sorbic acid, alcohols (e.g. phenyl ethyl alcohol), parabens (e.g., methylparaben, polyparaben), chlorhexidine, quaternary ammonium compounds, polyquaternium-1 (Polyquad®) Purite®, stabilized oxychloro complexes, Sofzia®, sodium perborate (GenAqua®), cetrimonium chloride, edetat disodium, thimerosal, etc. In some embodiments, a formulation of the disclosure does not include a preservative.

The present disclosure provides salts of any one or both of a therapeutic agent and a preservative. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt.

Metal salts can arise from the addition of an inorganic base to a compound of the present disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is an ammonium salt, a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the present disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, an imidazole salt, or a pyrazine salt.

Acid addition salts can arise from the addition of an acid to a compound of the present disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

The methods and formulations described herein include the use of amorphous forms as well as crystalline forms (also known as polymorphs). Active metabolites of compounds or salts of any one of the compounds of the present disclosure having the same type of activity are included in the scope of the present disclosure. In addition, the compounds described herein can exist in unsolvated as well as solvated forms with pharmaceutically acceptable solvents such as water, ethanol, and the like. The solvated forms of the compounds and salts presented herein are also considered to be disclosed herein.

Solution, Emulsion, or Suspension

Provided herein are pharmaceutical formulations which may comprise a solution, emulsion, or suspension of a therapeutic agent and a preservative. In some embodiments, provided herein are compositions comprising a therapeutically effective amount of any compound or salt of any one of the preservatives and/or therapeutic agents of the present disclosure. In some embodiments, a therapeutic solution, emulsion, or suspension may be used in any of the methods described herein. The solution, emulsion, or suspension may additionally comprise one or more pharmaceutically acceptable excipients. Table 1 to Table 4 provide examples of pharmaceutical formulations which may be used with any embodiment of the apparatuses and methods for removing a preservative disclosed herein.

In some embodiments, a compound of preservative and/or therapeutic agent may be used for the treatment of a therapeutic disorder such as, dry eye, bacterial infection, glaucoma, hypertension, inflammation, allergic conjunctivitis, hypotrichosis of the eyelashes, fungal infection, etc. Additionally or alternatively, a compound of a preservative and/or therapeutic agent may be used during a preventative, diagnostic, or therapeutic ophthalmological procedure, for example, local anesthetic, pupil dilation, etc. A formulation administered to the eye may be administered topically, for example, with an eye drop. In some embodiments, the compounds or salts of the disclosure with low aqueous solubility may preferentially be formulated as aqueous suspensions.

In some embodiments, formulations of the disclosure comprise a compound or salt of any one of the therapeutic agent and/or the preservative of the present disclosure, wherein the compound or salt is largely free of impurities, such as at least about 80 wt % pure, at least about 81% pure, at least about 82% pure, at least about 83% pure, at least about 84% pure, at least about 85% pure, at least about 86% pure, at least about 87% pure, at least about 88% pure, at least about 89% pure, at least about 90% pure, at least about 91% pure, at least about 92% pure, at least about 93% pure, at least about 94% pure, at least about 95% pure, at least about 96% pure, at least about 97% pure, at least about 98% pure, at least about 99% pure, at least about 99.1% pure, at least about 99.2% pure, at least about 99.3% pure, at least about 99.4% pure, at least about 99.5% pure, at least about 99.6% pure, at least about 99.7% pure, at least about 99.8% pure, or at least about 99.9% pure.

In some embodiments, formulations of the disclosure comprise a compound or salt of any one of the therapeutic agent and/or the preservative of the present disclosure, wherein the compound or salt is about 70% to about 99.99%, about 80% to about 99.9%, about 85% to about 99%, about 90% to about 99%, about 95% to about 99%, about 97% to about 99%, about 98% to about 99%, about 98% to about 99.9%, about 99% to about 99.99%, about 99.5% to about 99.99%, about 99.6% to about 99.99%, about 99.8 to about 99.99%, or about 99.9% to about 99.99% free of impurities.

The amount of the compound or salt in a solution, emulsion, or suspension of the present disclosure can be measured as a percentage of mass per volume. In some embodiments, a solution, emulsion, or suspension such as an aqueous solution of the disclosure, comprises from about 0.05 wt % to about 10 wt % of the compound or salt of any one of the therapeutic agents disclosed herein. In some embodiments, a solution, emulsion, or suspension such as an aqueous solution of the disclosure, comprises about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 2.1 wt %, about 2.2 wt %, about 2.3 wt %, about 2.4 wt %, about 2.5 wt %, about 2.6 wt %, about 2.7 wt %, about 2.8 wt %, about 2.9 wt %, about 3 wt %, about 3.1 wt %, about 3.2 wt %, about 3.3 wt %, about 3.4 wt %, about 3.5 wt %, about 3.6 wt %, about 3.7 wt %, about 3.8 wt %, about 3.9 wt %, about 4 wt %, about 4.1 wt %, about 4.2 wt %, about 4.3 wt %, about 4.4 wt %, about 4.5 wt %, about 5 wt %, about 6 wt %, about 7 wt %, about 8 wt %, about 9 wt %, or about 10 wt % of a compound or salt of the therapeutic agent described herein.

A compound or salt of the therapeutic agent described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a therapeutic agent described herein may be present in a solution, emulsion, or suspension within a range of concentrations, the range being defined by an upper and lower value selected from any of the preceding concentrations. For example, the compound or salt of a therapeutic agent of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

In some embodiments, a solution, emulsion, or suspension such as an aqueous solution of the disclosure, comprises from about 0.001 wt % to about 0.3 wt % of the compound or salt of any one of the preservatives disclosed herein. In some embodiments, a solution, emulsion, or suspension such as an aqueous solution of the disclosure, comprises about 0.001 wt %, about 0.002 wt %, about 0.003 wt %, about 0.004 wt %, about 0.005 wt %, about 0.006 wt %, about 0.007 wt %, about 0.008 wt %, about 0.009 wt %, about 0.01 wt %, about 0.02 wt %, about 0.03 wt %, about 0.04 wt %, about 0.05 wt %, about 0.06 wt %, about 0.07 wt %, about 0.08 wt %, about 0.09 wt %, about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, about 1 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2 wt %, about 3 wt %, about 4 wt %, about 5 wt %, about 6 wt %, about 7 wt %, about 8 wt %, about 9 wt %, or about 10 wt % of a compound or salt of the preservative described herein.

A compound or salt of the preservative described herein can be present in a solution, emulsion, or suspension of the present disclosure at a concentration of, for example, about 500 nM, about 600 nM, about 700 nM, about 800 nM, about 900 nM, about 1 µM, about 2 µM, about 3 µM, about 4 µM, about 5 µM, about 6 µM, about 7 µM, about 8 µM, about 9 µM, about 10 µM, about 20 µM, about 30 µM, about 40 µM, about 50 µM, about 60 µM, about 70 µM, about 80 µM, about 90 µM, about 100 µM, about 150 µM, about 200 µM, about 250 µM, about 300 µM, about 350 µM, about 400 µM, about 450 µM, about 500 µM, about 550 µM, about 600 µM, about 650 µM, about 700 µM, about 750 µM, about 800 µM, about 850 µM, about 900 µM, about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM. The compound of a preservative described herein may be present in a composition within a range of concentrations, the range being defined by an upper and lower value selected from any of the preceding concentrations. For example, the compound or salt of a preservative of the disclosure may be present in the solution, emulsion, or suspension at a concentration of from about 1 nM to about 100 mM, about 10 nM to about 10 mM, about 100 nM to about 1 mM, about 500 nM to about 1 mM, about 1 mM to about 50 mM, about 10 mM to about 40 mM, about 20 mM to about 35 mM, or about 20 mM to about 30 mM.

In some embodiments, an aqueous solutions, emulsions, or suspensions of the disclosure comprises at least 90 wt % water, such as at least 91 wt %, at least 92 wt %, at least 93 wt %, at least 94 wt %, at least 95 wt %, at least 96 wt %, at least 97 wt %, at least 98 wt %, or even at least 99 wt % of water.

In some embodiments, a solution, emulsion, or suspension of the present disclosure comprises an agent for adjusting the pH of the formulation. In some embodiments, the agent for adjusting the pH could be an acid, e.g., hydrochloric acid or boric acid, or a base, e.g., sodium hydroxide or potassium hydroxide. In some embodiments, the agent for adjusting the pH is an acid such as boric acid. The formulation may comprise about 0.05 wt % to about 5 wt %, about 0.1% to about 4%, about 0.1% to about 3 wt %, about 0.1 wt % to about 2 wt %, or about 0.1 wt % to about 1 wt % of an agent for adjusting the pH.

Solutions, emulsions, or suspensions of the disclosure can be formulated at any suitable pH. In some embodiments, the pH of the solution emulsion or suspension is about 4, about 4.05, about 4.1, about 4.15, about 4.2, about 4.25, about 4.3, about 4.35, about 4.4, about 4.45, about 4.5, about 4.55, about 4.6, about 4.65, about 4.7, about 4.75, about 4.8, about 4.85, about 4.9, about 4.95, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9 pH units. In some embodiments, the pH of the solution, emulsion, or suspension is from about 4 to about 10, about 4.75 to about 7.40, about 5 to about 9, about 6 to about 8, about 6.5 to about 8, about 7 to about 8, about 7.2 to about 8, about 7.2 to about 7.8, about 7.3 to about 7.5, or about 7.35 to about 7.45. In some embodiments the pH of the solution, emulsion, or suspension is about 7.4.

In some embodiments, solutions, emulsions, or suspensions of the present disclosure further comprise one or more physiologically acceptable carriers including excipients and auxiliaries which facilitate processing of the pharmaceutical agent into preparations which are used pharmaceutically. Proper formulation is dependent upon the route of administration chosen.

In some embodiments, the addition of an excipient to a pharmaceutical formulation of the present disclosure can increase or decrease the viscosity of the composition by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. An excipient which changes a viscosity may be polyvinyl alcohol, polyvinyl pryolidone, methyl cellulose, hydroxy propyl methylcellulose, hydroxyethyl cellulose, carboxymethyl cellulose, hydroxy propyl cellulose, etc. In some embodiments, the addition of an excipient to a pharmaceutical formulation of the present disclosure can increase or decrease the viscosity of the composition by no greater than 5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, no greater than 95%, or no greater than 99%. Examples of ranges which the viscosity change falls within can be created by combining any two of the preceding percentages. For example the addition of an excipient can increase or decrease the viscosity of the composition by 5% to 99%, by 10% to 95%, by 20% to 70% or by 35% to 55%.

In some embodiments, an excipient that increases a viscosity may comprise polyvinyl alcohol, poloxamers, hyaluronic acid, carbomers, and polysaccharides, that is, cellulose derivatives, gellan gum, and xanthan gum. In some embodiments, an excipient that increases mucoadhesive properties may be added. Excipients that increase mucoadhesion may include polyacrylic acid, hyaluronic acid, sodium carboxymethyl cellulose, lectins, and chitosan.

In some embodiments, solutions, emulsions, or suspensions of the present disclosure further comprise an agent for adjusting the osmolarity of the solution, emulsion, or suspension, e.g., mannitol, sodium chloride, sodium sulfate, dextrose, potassium chloride, glycerin, propylene glycol, calcium chloride, and magnesium chloride. In some embodiments, the solution, emulsion, or suspension comprises from about 0.1 wt % to about 10 wt %, about 0.5 wt % to about 8 wt %, about 1 wt % to about 5 wt %, about 1 wt % to about 4 wt %, or about 1 wt % to about 3 wt % of an agent for adjusting the osmolarity of the solution, emulsion, or suspension. In some embodiments, the solution, emulsion, or suspension of the disclosure has an osmolarity from about 10 mOsm to about 1000 mOsm, about 100 mOsm to about 700 mOsm, about 200 mOsm to about 400 mOsm, about 250 mOsm to about 350 mOsm or even about 290 mOsm to about 310 mOsm.

In some embodiments, solutions, emulsions, or suspensions of the present disclosure further comprise a buffering agent, such as tromethamine, potassium phosphate, sodium phosphate, saline sodium citrate buffer (SSC), acetate, saline, physiological saline, phosphate buffer saline (PBS), 4-2-hydroxyethyl-1-piperazineethanesulfonic acid buffer (HEPES), 3-(N-morpholino)propanesulfonic acid buffer (MOPS), and piperazine-N,N'-bis(2-ethanesulfonic acid) buffer (PIPES), sodium acetate-boric acid stock solution, boric acid-sodium carbonate with sodium chloride solution, boric acid-sodium borate buffer, sodium and potassium phosphate buffers, boric acid-sodium carbonate with potassium chloride, or combinations thereof. In some embodiments, the solution, emulsion, or suspension comprises from about 0.05 wt % to about 5 wt %, about 0.1 wt % to about 4 wt %, about 0.1 wt % to about 3 wt %, about 0.1 wt % to about 2 wt %, or about 0.1 wt % to about 1 wt % of an agent for buffering the solution, emulsion, or suspension.

In some embodiments, solutions, emulsions, or suspensions of the present disclosure further comprise a solubilizing agent. In some embodiments, the compound or salt of a preservative or a therapeutic agent of the disclosure exhibits low aqueous solubility and the addition of a solubilizing agent enhances the solubility of the compound or salt. A solubilizing agent may be a surfactant, a co-solvent, etc. In some embodiments, the solution, emulsion, or suspension comprises from about 2 wt % to about 15 wt % of a solubilizing agent, about 3 wt % to about 12 wt %, about 4 wt % to about 10 wt %, about 5 wt % to about 10 wt %, or about 6 wt % to about 10 wt % of a solubilizing agent, e.g., a cyclodextrin, polysorbate 20, 60, and 80, Pluronic F68, F-84 and P-103. In some embodiments, the solution, emulsion, or suspension is an aqueous solution comprising a solubilizing agent. In some embodiments, a solution, emulsion, or suspension for topical administration to the eye comprises a solubilizing agent.

In some embodiments, the solutions, emulsions, or suspensions of the disclosure may include one or more additional excipients. The amount of the excipient in a pharmaceutical formulation of the disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 60%, about 70%, about 80%, about 90%, about 100%, about 200%, about 300%, about 400%, about 500%, about 600%, about 700%, about 800%, about 900%, or about 1000% by mass of the compound in the solution, emulsion, or suspension. The amount of the excipient in a solution, emulsion, or suspension of the disclosure can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass of the compound in the solution, emulsion, or suspension.

The amount of the excipient in a solution, emulsion, or suspension of the present disclosure can be about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.5%, about 2%, about 2.5%, about 3%, about 3.5%, about 4%, about 4.5%, about 5%, about 6%, about 7%, about 8%, about 9%, about 10%, about 15%, about 20%, about 25%, about 30%, about 35%, about 40%, about 45%, about 50%, about 55% about 60%, about 65%, about 70%, about 75%, about 80%, about 85%, about 90%, about 95%, about 99%, or about 100% by mass or by volume of the unit dosage form. The amount of the excipient in a solution, emulsion, or suspension can be between 0.01% and 1000%, between 0.02% and 500%, between 0.1% and 100%, between 1% and 50%, between 0.01% and 1%, between 1% and 10%, between 10% and 100%, between 50% and 150%, between 100% and 500%, or between 500% and 1000% by mass or by volume of the unit dosage form.

The ratio of a compound of a therapeutic agent of the present disclosure to an excipient in a pharmaceutical formulation of the present disclosure can be about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1 about 30:about 1, about 25:about 1, about 20:about 1, about 15:about 1, about 10:about 1, about 9:about 1, about 8:about 1, about 7:about 1, about 6:about 1, about 5:about 1, about 4:about 1, about 3:about 1, about 2:about 1, about 1:about 1, about 1:about 2, about 1:about 3, about 1:about 4, about 1:about 5, about 1:about 6, about 1:about 7, about 1:about 8, about 1:about 9, or about 1:about 10. The ratio of a compound of a therapeutic agent to an excipient in a solution, emulsion, or suspension of the present disclosure can be within the range of between about 100:about 1 and about 1 to about 10, between about 10:about 1 and about 1:about 1, between about 5:about 1 and about 2:about 1.

Pharmaceutically acceptable carriers are well known in the art and include, for example, aqueous solutions such as water or physiologically buffered saline or other solvents or vehicles such as glycols, glycerol, oils such as olive oil, or organic esters. The excipients can be chosen, for example, to effect delayed release of an agent or to selectively target one or more cells, tissues or organs. The composition can also be present in a solution suitable for topical administration, such as an eye drop.

In some embodiments, the solution emulsion or suspension provided herein comprises an alcohol as an excipient. Non-limiting examples of alcohols include ethanol, propylene glycol, glycerol, polyethylene glycol, chlorobutanol, isopropanol, xylitol, sorbitol, maltitol, erythritol, threitol, arabitol, ribitol, mannitol, galactilol, fucitol, lactitol, and combinations thereof.

Methods for the preparation of compositions comprising the compounds described herein can include formulating the compounds with one or more inert, pharmaceutically-acceptable excipients. Liquid compositions include, for example, solutions in which a compound is dissolved, emulsions comprising a compound, or a solution containing liposomes, micelles, or nanoparticles comprising a compound as disclosed herein. These compositions can also contain minor amounts of nontoxic, auxiliary substances, such as wetting or emulsifying agents, pH buffering agents, and other pharmaceutically-acceptable additives.

The present disclosure further comprises articles of manufacture comprising packaging material, a nozzle of the present disclosure, and, optionally, a formulation comprising a therapeutically effective amount of a therapeutic agent and a preservative, and wherein the packaging material comprises a label which indicates the therapeutic agent.

Definitions

Unless defined otherwise, all technical and scientific terms used herein have the same meaning as is commonly understood by one of skill in the art to which this invention belongs. All patents and publications referred to herein are incorporated by reference.

As used in the specification and claims, the singular form "a", "an" and "the" includes plural references unless the context clearly dictates otherwise.

As used herein, and unless otherwise specified, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range. In certain embodiments, the term "about" or "approximately" means within 40.0 mm, 30.0 mm, 20.0 mm, 10.0 mm 5.0 mm 1.0 mm, 0.9 mm, 0.8 mm, 0.7 mm, 0.6 mm, 0.5 mm, 0.4 mm, 0.3 mm, 0.2 mm or 0.1 mm of a given value or range.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

In some embodiments, the pharmaceutically acceptable base addition salt is chosen from ammonium, potassium, sodium, calcium, and magnesium salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier is "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In some embodiments, the term "prevent" or "preventing" as related to a disease or disorder may refer to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms may be based on objective or subjective parameters; including the results of a physical examination, neuropsychiatric exams, and/or a psychiatric evaluation. The term "treating" and conjugations thereof, include prevention of an injury, pathology, condition, or disease.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of a "therapeutically effective amount" is an amount sufficient to contribute to the treatment, prevention, or reduction of a symptom or symptoms of a disease, which could also be referred to as a "therapeutically effective amount." A "reduction of" a symptom or symptoms (and grammatical equivalents of this phrase) means decreasing of the severity or frequency of the symptom(s), or elimination of the symptom(s). The exact amounts may depend on the purpose of the treatment, and may be ascertainable by one skilled in the art using known techniques.

The dosage and frequency (single or multiple doses) administered to a mammal may vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents may be used in conjunction with the methods and compounds of this disclosre. Adjustment and manipulation of established dosages (e.g., frequency and duration) are well within the ability of those skilled in the art.

Dosages may be varied depending upon the requirements of the patient and the compound being employed. The dose administered to a patient, in the context of the present disclosure should be sufficient to affect a beneficial therapeutic response in the patient over time. The size of the dose also may be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals may be adjusted individually to provide levels of the administered compound effective for the particular clinical indication being treated. This may provide a therapeutic regimen that is commensurate with the severity of the individual's disease state.

Compounds of the present disclosure also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Examples

It is understood that the examples and embodiments described herein are for illustrative purposes only and are not intended to limit the scope of the claimed invention. It is also understood that various modifications or changes in light of the examples and embodiments described herein will be suggested to persons skilled in the art and are to be include within the spirit and purview of this application and scope of the appended claims.

Figure 18:
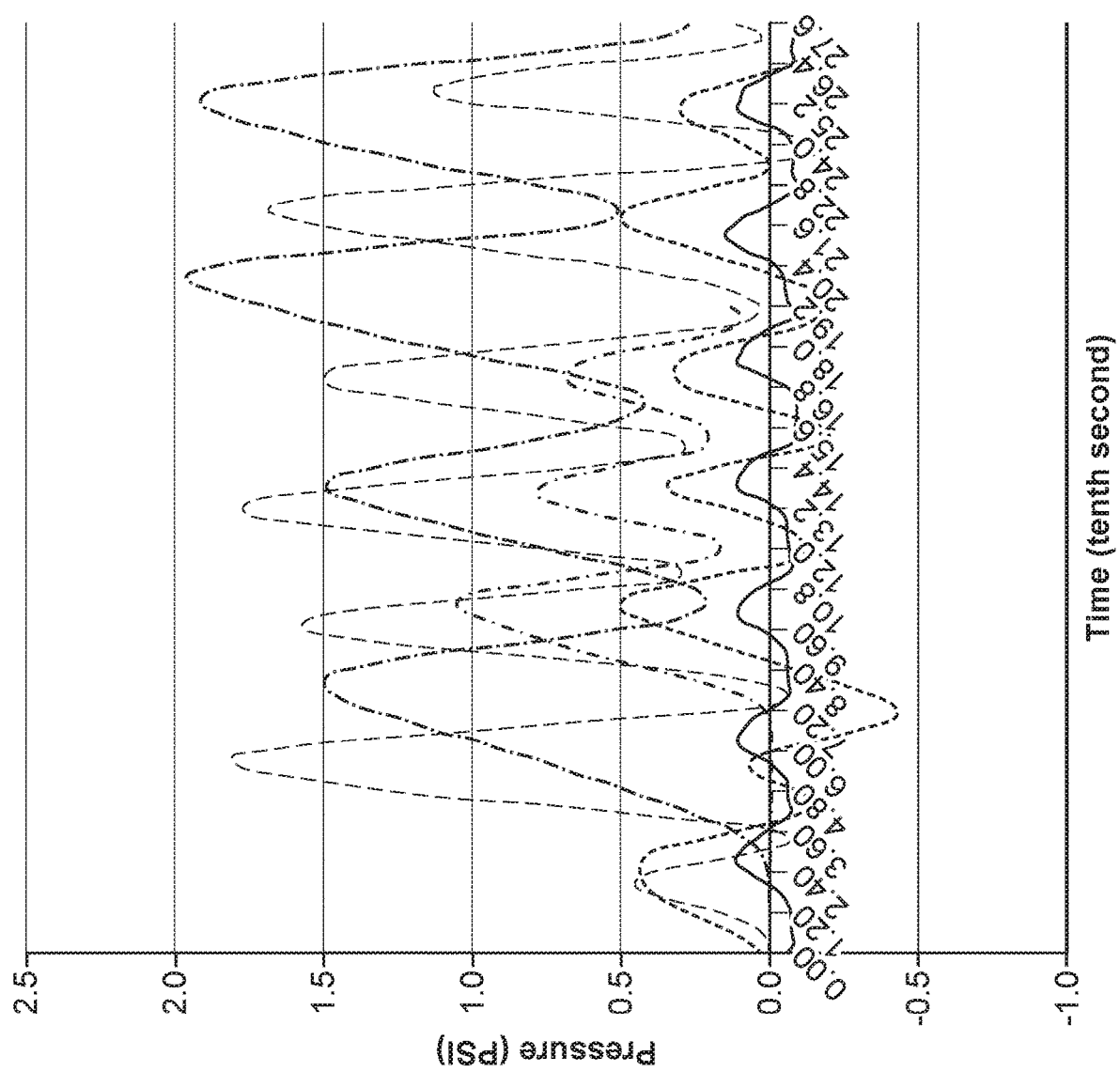
FIG. 18 shows a plot of squeeze pressure versus time for five example flow diverters during drop formation.

FIG. 18 shows a plot of the pressure due to squeezing the bottle (PSI) as measured inside the bottle versus time (tenth seconds) for five example flow diverters during drop formation. As shown in FIG. 18, a control comprises a commercially available squeeze bottle with 0.16 g of a pHEMA matrix with moderate compaction disposed in the tip. Average squeeze pressure for the control was 0.1 PSI (0.007 Atm). The sachet geometry comprises 0.299 g of a 25% pHEMA and 75% TBMA matrix disposed in an insert with moderate compaction. Average squeeze pressure for the sachet geometry was 1.75 PSI (0.12 Atm). The concentric geometry comprises 0.158 g of a 25% pHEMA and 75% TBMA matrix disposed within the flow diverter with moderate compaction. Average squeeze pressure for the concentric geometry was 2.00 PSI (0.14). The dart geometry comprises 0.161 g of a 25% pHema and 75% TBMA matrix disposed within the flow diverter with moderate compaction. Average squeeze pressure for the dart geometry was 0.50 PSI (0.034 Atm). The nautilus geometry comprises 0.153 g of a 25% pHema and 75% TBMA matrix disposed with the flow diverter with moderate compaction. Average squeeze pressure for the nautilus geometry was 1.00 PSI (0.68 Atm). Typical drop formation times for the flow geometries in the illustrated examples are 3-7 seconds; however, time to form drop may be shorter if pressure increases more quickly. Firmer compaction may be expected to increase squeeze pressures and drop formation times. Weaker compaction may be expected to decrease squeeze pressure and drop formation times.

Illustrative solutions, emulsions, or suspensions which can be used in aspects of the pharmaceutical formulation disclosed herein are shown in Tables 1 to 4. Example solutions, emulsions, or suspensions in the table below may be integrated into nozzles and nozzle systems of the present disclosure. One or more embodiments, variations, and examples of the nozzles, nozzle systems, and geometries described herein may be incorporated into an eye drop dispensing system, which system may comprise a squeezable bottle. A squeezable bottle may comprise a reservoir in which a fluid may be stored. A fluid stored in the reservoir may comprise an embodiment, variation, or example of solutions, emulsions, or suspensions described herein, including those examples provided in Tables 1 to 4.

TABLE 1

| | | | | | |
|---|---|---|---|---|---|
| | Pharmaceuticals Sorted by Indication |
| Market Name | Drug | % Active Ingredient | Formulation Type | Indication | Preservative |
| | Dry Eye |
| Restasis | cyclosporine | 0.05% | emulsion | keratoconjunctivitis sicca | none |
| Xiidra | lifitegrast | 5% | solution | keratoconjunctivitis sicca | none |
| Visine | Tetrahydozoline | | | keratoconjunctivitis sicca | |
| | Bacterial Infection |
| Bleph 10 | sulfacetamide sodium | 10% | solution | conjunctivitis and other ocular infections | benzalkonium chloride 0.005% |
| Blephamide | sulfacetamide sodium-prednisolone acetate | 10%/0.2% | suspension | bacterial ocular infection | benzalkonium chloride 0.004% |
| Ocuflox | ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo-conjunctivitis | benzalkonium chloride 0.04 mg/mL |
| Zymaxid | gatifloxacin | 0.3% and 0.5% | solution | bacterial conjunctivitis | benzalkonium chloride 0.005% |
| Zymar | gatifloxacin | 0.3% | solution | bacterial conjunctivitis | benzalkonium chloride 0.005%; |
| Ciloxan | ciprofloxacin | 0.3% | solution | bacterial conjunctivitis | None |
| Moxeza | moxifloxacin | 0.5% | solution | bacterial conjunctivitis | none |
| Tobrex | tobramycin | 0.3% | solution | infections of the eye and its adnexa caused by susceptible bacteria | benzalkonium chloride 0.01% |
| Vigamox | moxifloxacin | 0.5% | solution | bacterial conjunctivitis | none |
| Iquix | levofloxacin | 1.5% | solution | bacterial conjunctivitis | benzalkonium chloride 0.005% |
| Quixin | levofloxacin | 0.5% | solution | bacterial conjunctivitis | benzalkonium chloride 0.005% |
| | Glaucoma or Hypertension |
| Alphagan | brimonidine tartrate | 0.01% | solution | open-angle glaucoma or ocular hypertension | Purite ® 0.005% (0.05 mg/mL) |
| Lumigan | bimatroprost | 0.01% | solution | open angle glaucoma or ocular hypertension | benzalkonium chloride 0.2 mg/mL |
| Betagan | levobunolol hydrochloride | 0.5% | solution | chronic open-angle glaucoma or ocular hypertension | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled IOP | benzalkonium chloride 0.005% |
| Azopt | brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |

TABLE 1-continued

Pharmaceuticals Sorted by Indication

| Market Name | Drug | % Active Ingredient | Formulation Type | Indication | Preservative |
|---|---|---|---|---|---|
| Isopto Carpine | pilocarpine hydrochloride | 1%, 2% and 4% | solution | IOP reduction; open-angle glaucoma or ocular hypertension; acute angle-closure glaucoma; induction of miosis | benzalkonium chloride 0.01% |
| Iopidine | apraclonidine | 0.5% and 1.0% | solution | Short term adjunctive therapy in patients on maximally tolerated medical therapy who require additional IOP reduction | benzalkonium chloride 0.01% |
| Simbrinza | brinzolamide/ brimonidine tartrate | 1%/0.2% | suspension | reduction of elevated IOP in patients with open-angle glaucoma or ocular hypertension | benzalkonium chloride 0.03 mg |
| Travatan Z | travoprost | 0.004% | solution | open-angle glaucoma or ocular hypertension who are intolerant of other intraocular pressure lowering medications | ionic buffered system, sofZia |
| Isralol | Timolol maleate | 0.5% | solution | ocular hypertension or open-angle glaucoma | benzalkonium chloride 0.05 mg/mL |
| Xalatan | latanoprost | approximately 1.5 µg per drop | solution | open-angle glaucoma or ocular hypertension | benzalkonium chloride, 0.02% |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | tafluprost | 0.0015% | solution | open-angle glaucoma or ocular hypertension | none |
| Vesneo | Latanoprostene Bunod | | | Glaucoma | |
| Vyzulta | Latanoprostene Bunod | | | Glaucoma | |
| Cosopt | Dorzolamide + Timolol | | | Glaucoma | |
| Inflammation | | | | | |
| Acular LS | ketorolac tromethamine | 0.4% | solution | ocular pain and burning/stinging following corneal refractive surgery | benzalkonium chloride 0.006% |
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| FML Forte | fluorometholone | 0.25% | ointment | corticosteroid-responsive inflammation of the palpebral and bulbar conjunctiva, cornea and anterior segment of the globe | benzalkonium chloride 0.005% |
| FML | fluorometholone | 0.1% | suspension | corticosteroid-responsive inflammation of the palpebral and bulbar conjunctiva, cornea and anterior segment of the globe | benzalkonium chloride 0.004% |

TABLE 1-continued

Pharmaceuticals Sorted by Indication

| Market Name | Drug | % Active Ingredient | Formulation Type | Indication | Preservative |
|---|---|---|---|---|---|
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |
| Pred-G | gentamicin and prednisolone acetate | 0.3%/1% | suspension | steroid-responsive inflammatory; bacterial infection; thermal burns or penetration of foreign bodies | Benzalkonium chloride 0.005% |
| Durezol | difluprednate | 0.05% | emulsion | inflammation and pain associated with ocular surgery | sorbic acid 0.1% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | nepafenac | 0.3% | suspension | pain and inflammation associated with cataract surgery | benzalkonium chloride 0.005% |
| Maxidex | dexamethasone | 0.1% | suspension | Steroid responsive inflammatory conditions; corneal injury from chemical, radiation, or thermal burns, or penetration of foreign bodies | benzalkonium chloride 0.01% |
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Nevanac | nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Voltaren Ophthalmic | diclofenac sodium | 0.1% | solution | inflammation from cataract extraction; temporary relief of pain and photophobia following corneal refractive surgery | None |

TABLE 1-continued

Pharmaceuticals Sorted by Indication

| Market Name | Drug | % Active Ingredient | Formulation Type | Indication | Preservative |
|---|---|---|---|---|---|
| Bromday | bromfenac | 0.09% | solution | postoperative inflammation in patients who have undergone cataract extraction | benzalkonium chloride 0.05 mg/mL |
| Xibrom | bromfenac | 0.09% | solution | postoperative inflammation in patients who have undergone cataract extraction | benzalkonium chloride (0.05 mg/mL) |
| Xibrom | bromfenac | 0.09% | solution | postoperative inflammation in patients who have undergone cataract extraction | benzalkonium chloride 0.05 mg/mL |
| Allergic Conjunctivitis | | | | | |
| Alocril | nedocromil sodium | 2% | solution | itching associated with allergic conjunctivitis | benzalkonium chloride 0.01% |
| Elestat | epinastine HCl | 0.05% | suspension | itching associated with allergic conjunctivitis | Benzalkonium chloride 0.01%; |
| Lastacaft | alcaftadine | 0.25% | solution | itching associated with allergic conjunctivitis | benzalkonium chloride 0.005% |
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Emadine | emedastine difumarate | 0.5% | solution | allergic conjunctivitis | benzalkonium chloride, 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Hair Growth | | | | | |
| Latisse | bimatoprost | 0.03% | solution | hypotrichosis of the eyelashes | benzalkonium chloride 0.05 mg/mL |
| Local Anesthetic | | | | | |
| Alcaine | proparacaine hydrochloride | 0.5% | solution | topical anesthesia - removal of foreign bodies; measurement of intraocular pressure; conjunctive scraping | benzalkonium chloride 0.01% |
| Tetracaine | Tetracaine hydrochloride | 0.5% | solution | procedures requiring a rapid and short acting topical ophthalmic anesthetic | None |
| Pupil Dilation | | | | | |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | Benzalkonium chloride 0.1 mg in 1.0 mL |
| Cyclomydril | cyclopentolate hydrochloride and phenylephrine hydrochloride | 0.2%/1.0% | solution | For the production of mydriasis (pupil dilation) | Benzalkonium chloride 0.01% |

TABLE 1-continued

Pharmaceuticals Sorted by Indication

| Market Name | Drug | % Active Ingredient | Formulation Type | Indication | Preservative |
|---|---|---|---|---|---|
| Isopto Atropine | atropine sulfate | 1% | solution | mydriasis; cycloplegia; penalization of the healthy eye in the treatment of amblyopia | benzalkonium chloride 0.01% |
| Mydriacyl | tropicamide | 0.5% or 1.0% | solution | mydriasis and cycloplegia | benzalkonium chloride 0.01% |
| Fungal infection | | | | | |
| Natacyn | natamycin | 5% | suspension | anti-fungal; fungal blepharitis, conjunctivitis, and keratitis | benzalkonium chloride 0.02% |

TABLE 2

Experimental Presbyopia Formulations.

| Drug Code | Drug | % Active Ingredient | Formulation Type | Indication | Preservative |
|---|---|---|---|---|---|
| Presbyopia | | | | | |
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| CSF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| AAGN-199201 | Pilocarpine and/or oxymetazoline | 0.1%-1% | Solution or suspension | presbyopia | Any, benzalkonium chloride, 0.01% |
| AAGN-190584 | keterolac | 0.1%-1% | Solution or suspension | presbyopia | Any, benzalkonium chloride, 0.01% |

TABLE 3

Additional Pharmaceuticals

| Market Name | Drug | % Active Ingredient | Formulation Type | Indication | Preservative |
|---|---|---|---|---|---|
| Restasis | cyclosporine | 0.05% | emulsion | keratoconjunctivitis sicca | none |
| Latisse | bimatoprost | 0.03% | solution | hypotrichosis of the eyelashes | benzalkonium chloride 0.05 mg/mL |
| Alphagan | brimonidine Tartrate | 0.01% | solution | open-angle glaucoma or ocular hypertension | Purite ® 0.005% (0.05 mg/mL) |
| Lumigan | bimatroprost | 0.01% | solution | open angle glaucoma or ocular hypertension | benzalkonium chloride 0.2 mg/mL |
| Acular LS | ketorolac tromethamine | 0.4% | solution | ocular pain and burning/stinging following corneal refractive surgery | benzalkonium chloride 0.006% |

TABLE 3-continued

Additional Pharmaceuticals

| Market Name | Drug | % Active Ingredient | Formulation Type | Indication | Preservative |
|---|---|---|---|---|---|
| Acular | ketorolac tromethamine | 0.5% | solution | inflammation following cataract surgery; relief of ocular itching due to seasonal allergic conjunctivitis | benzalkonium chloride 0.01% |
| Acuvail | ketorolac tromethamine | 0.45% | solution | treatment of pain and inflammation following cataract surgery | none |
| Alocril | nedocromil sodium | 2% | solution | itching associated with allergic conjunctivitis | benzalkonium chloride 0.01% |
| Betagan | levobunolol hydrochloride | 0.5% | solution | chronic open-angle glaucoma or ocular hypertension | benzalkonium chloride 0.004% |
| Bleph 10 | sulfacetamide sodium | 10% | solution | conjunctivitis and other ocular infections | benzalkonium chloride 0.005% |
| Blephamide | sulfacetamide sodium - prednisolone acetate | 10%/0.2% | suspension | bacterial ocular infection | benzalkonium chloride 0.004% |
| Combigan | brimonidine tartrate/timolol maleate | 0.2%/0.5% | solution | glaucoma or ocular hypertension who require adjunctive or replacement therapy due to inadequately controlled iop | benzalkonium chloride 0.005% |
| Elestat | epinastine HCl | 0.05% | suspension | itching associated with allergic conjunctivitis | benzalkonium chloride 0.01%; |
| FML Forte | fluorometholone | 0.25% | ointment | corticosteroid-responsive inflammation of the palpebral and bulbar conjunctiva, cornea and anterior segment of the globe | benzalkonium chloride 0.005% |
| FML | fluorometholone | 0.1% | suspension | corticosteroid-responsive inflammation of the palpebral and bulbar conjunctiva, cornea and anterior segment of the globe | benzalkonium chloride 0.004% |
| Lastacaft | alcaftadine | 0.25% | solution | itching associated with allergic conjunctivitis | benzalkonium chloride 0.005% |
| Ocuflox | ofloxacin | 0.3% | solution | bacterial ocular infection; corneal ulcers | benzalkonium chloride (0.005%) |
| Polytrim | polymyxin B sulfate and trimethoprim | polymyxin B sulfate 10,000 units/mL; trimethoprim sulfate equivalent to 1 mg/mL | solution | ocular bacterial infections; conjunctivitis; blepharo-conjunctivitis | benzalkonium chloride 0.04 mg/mL |
| Pred Forte | prednisolone acetate | 1% | suspension | steroid-responsive inflammation of the palpebral and bulbar conjunctiva, cornea, and anterior segment of the globe | benzalkonium chloride |
| Pred Mild | prednisolone acetate | 0.12% | suspension | mild to moderate noninfectious allergic and inflammatory disorders of the lid, conjunctiva, cornea, and sclera, including chemical and thermal burns | benzalkonium chloride |

TABLE 3-continued

Additional Pharmaceuticals

| Market Name | Drug | % Active Ingredient | Formulation Type | Indication | Preservative |
|---|---|---|---|---|---|
| Pred-G | gentamicin and prednisolone acetate | 0.3%/1% | suspension | steroid-responsive inflammatory; bacterial infection; thermal burns or penetration of foreign bodies | benzalkonium chloride 0.005% |
| Zymaxid | gatifloxacin | 0.3% and 0.5% | solution | bacterial conjunctivitis | benzalkonium chloride 0.005% |
| Zymar | gatifloxacin | 0.3% | solution | bacterial conjunctivitis | benzalkonium chloride 0.005%; |
| Alcaine | proparacaine hydrochloride | 0.5% | solution | topical anesthesia - removal of foreign bodies; measurement of intraocular pressure; conjunctive scraping | benzalkonium chloride 0.01% |
| Alomide | lodoxamide tromethamine | 0.1% | solution | vernal keratoconjunctivitis; giant papillary conjunctivitis; allergic/atopic conjunctivitis | benzalkonium chloride 0.007% w/v |
| Azopt | brinzolamide | 1% | suspension | ocular hypertension or open-angle glaucoma | benzalkonium chloride 0.1 mg |
| Betoptic S | betaxolol hydrochloride | 0.25% and 0.5% | suspension | ocular hypertension or chronic open angle glaucoma | benzalkonium chloride 0.1 mg in 1 mL |
| Ciloxan | ciprofloxacin | 0.3% | solution | bacterial conjunctivitis | None |
| Cyclogyl | cyclopentolate hydrochloride | 0.5%, 1.0% or 2.0% | solution | pre- and post-operative states when mydriasis is required and when a shorter acting mydriatic and cycloplegic is needed in the therapy of iridocyclitis | benzalkonium chloride 0.1 mg in 1.0 mL |
| Cyclomydril | cyclopentolate hydrochloride and phenylephrine hydrochloride | 0.2%/1.0% | solution | for the production of mydriasis (pupil dilation) | benzalkonium chloride 0.01% |
| Durezol | difluprednate | 0.05% | emulsion | inflammation and pain associated with ocular surgery | sorbic acid 0.1% |
| Emadine | emedastine difumarate | 0.5% | solution | allergic conjunctivitis | benzalkonium chloride, 0.01% |
| Flarex | fluorometholone acetate | 0.1% | suspension | steroid-responsive inflammatory conditions of the palpebral and bulbar conjunctiva, cornea and anterior segment of the eye | benzalkonium chloride 0.01% |
| Ilevro | nepafenac | 0.3% | suspension | pain and inflammation associated with cataract surgery | benzalkonium chloride 0.005% |
| Iopidine | apraclonidine | 0.5% and 1.0% | solution | short term adjunctive therapy in patients on maximally tolerated medical therapy who require additional iop reduction | benzalkonium chloride 0.01% |
| Isopto Atropine | atropine sulfate | 1% | solution | mydriasis; cycloplegia; penalization of the healthy eye in the treatment of amblyopia | benzalkonium chloride 0.01% |

TABLE 3-continued

Additional Pharmaceuticals

| Market Name | Drug | % Active Ingredient | Formulation Type | Indication | Preservative |
|---|---|---|---|---|---|
| Isopto Carpine | pilocarpine hydrochloride | 1%, 2% and 4% | solution | iop reduction; open-angle glaucoma or ocular hypertension; acute angle-closure glaucoma; induction of miosis | benzalkonium chloride 0.01% |
| Maxidex | dexamethasone | 0.1% | suspension | steroid responsive inflammatory conditions; corneal injury from chemical, radiation, or thermal burns, or penetration of foreign bodies | benzalkonium chloride 0.01% |
| Maxitrol | neomycin and polymyxin B sulfates and dexamethasone | neomycin sulfate equivalent to neomycin 3.5 mg, polymyxin B sulfate 10,000 units, dexamethasone 0.1% | solution | steroid-responsive inflammatory ocular conditions for which a corticosteroid is indicated and where bacterial infection or a risk of bacterial ocular infection exists | methylparaben 0.05%, propylparaben 0.01% |
| Moxeza | moxifloxacin | 0.5% | solution | bacterial conjunctivitis | None |
| Mydriacyl | tropicamide | 0.5% or 1.0% | solution | mydriasis and cycloplegia | benzalkonium chloride 0.01% |
| Natacyn | natamycin | 5% | suspension | anti-fungal; fungal blepharitis, conjunctivitis, and keratitis | benzalkonium chloride 0.02% |
| Nevanac | nepafenac | 0.1% | suspension | pain and inflammation associated with cataract surgery | benzalkonium chloride 0.005% |
| Omnipred | prednisolone acetate | 1.0% | suspension | steroid responsive inflammatory conditions; corneal injury from chemical, radiation, or thermal burns, or penetration of foreign bodies | benzalkonium chloride 0.01% |
| Pataday | olopatadine hydrochloride | 0.2% | solution | ocular itching associated with allergic conjunctivitis | benzalkonium chloride 0.01% |
| Pazeo | olopatadine hydrochloride | 0.7% | solution | ocular itching associated with allergic conjunctivitis | benzalkonium chloride 0.015% |
| Simbrinza | brinzolamide/ brimonidine tartrate | 1%/0.2% | suspension | reduction of elevated iop in patients with open-angle glaucoma or ocular hypertension | benzalkonium chloride 0.03 mg |
| Tetracaine | hydrochloride | 0.5% | solution | procedures requiring a rapid and shortacting topical ophthalmic anesthetic | None |
| Tobradex ST | tobramycin/ dexamethasone | 0.3%/0.05% | suspension | steroid-responsive inflammatory ocular conditions for which a corticosteroid is indicated and where superficial bacterial ocular infection exists | benzalkonium chloride 0.1 mg |
| Tobrex | tobramycin | 0.3% | solution | infections of the eye and its adnexa caused by susceptible bacteria | benzalkonium chloride 0.01% |
| Travatan Z | travoprost | 0.004% | solution | open-angle glaucoma or ocular hypertension who are intolerant of other intraocular pressure lowering medications | ionic buffered system, sofZia |

TABLE 3-continued

Additional Pharmaceuticals

| Market Name | Drug | % Active Ingredient | Formulation Type | Indication | Preservative |
|---|---|---|---|---|---|
| Vigamox | moxifloxacin | 0.5% | solution | bacterial conjunctivitis | None |
| Voltaren Ophthalmic | diclofenac sodium | 0.1% | solution | inflammation from cataract extraction; temporary relief of pain and photophobia following corneal refractive surgery | None |
| Trusopt | dorzolamide hydrochloride | 2% | solution | ocular hypertension or open-angle glaucoma | benzalkonium chloride 0.0075% |
| Timoptic | timolol maleate | 0.25% and 0.5% | solution | ocular hypertension or open-angle glaucoma | benzalkonium chloride |
| Ziotan | tafluprost | 0.0015% | solution | open-angle glaucoma or ocular hypertension | none |
| Xalatan | latanoprost | approximately 1.5 μg per drop | solution | open-angle glaucoma or ocular hypertension | benzalkonium chloride, 0.02% |
| Bromday | bromfenac | 0.09% | solution | postoperative inflammation in patients who have undergone cataract extraction | benzalkonium chloride 0.05 mg/mL |
| Isralol | timolol maleate | 0.5% | solution | ocular hypertension or open-angle glaucoma | benzalkonium chloride 0.05 mg/mL |
| Xibrom | bromfenac | 0.09% | solution | postoperative inflammation in patients who have undergone cataract extraction | benzalkonium chloride (0.05 mg/mL) |
| Iquix | levofloxacin | 1.5% | solution | bacterial conjunctivitis | benzalkonium chloride 0.005% |
| Quixin | levofloxacin | 0.5% | solution | bacterial conjunctivitis | benzalkonium chloride 0.005% |
| Xibrom | bromfenac | 0.09% | solution | postoperative inflammation in patients who have undergone cataract extraction | benzalkonium chloride 0.05 mg/mL |
| Xiidra | lifitegrast | 5% | solution | Dry Eye | None |

TABLE 4

Other Pharmaceuticals

| Code of Drug in Clinical Trial | Drug | % Active Ingredient | Formulation Type | Indication | Preservative |
|---|---|---|---|---|---|
| EV06/ UNR844 | lipoic acid choline ester chloride | 3.0% | solution | presbyopia | benzalkonium chloride, 0.01% |
| PRX-100 | aceclidine/ tropicamide | 0.25-2.0%/ 0.025-0.1% | Solution or suspension | presbyopia | benzalkonium chloride, 0.02% |
| SF-1 | sodium hyaluronate/ diclofenac sodium/ pilocarpine HCl | 0.1-0.9%/ 0.006-0.012%/ 0.2-0.4% | Solution or suspension | presbyopia | Any, benzalkonium chloride, 0.01% |
| ECF843 | ECF843 | 0.1%-1% | Solution or suspension | Dry eye | Any, benzalkonium chloride, 0.01% |

TABLE 4-continued

Other Pharmaceuticals

| Code of Drug in Clinical Trial | Drug | % Active Ingredient | Formulation Type | Indication | Preservative |
|---|---|---|---|---|---|
| None | rebamipide | 1%, 2% | solution | Dry eye (keratoconjunctivitis sicca) | Any, benzalkonium chloride, 0.01% |
| AAGN-199201 | Pilocarpine and/or oxymetazoline | 0.1%-1% | Solution or suspension | presbyopia | Any, benzalkonium chloride, 0.01% |
| AAGN-190584 | keterolac | 0.1%-1% | Solution or suspension | presbyopia | Any, benzalkonium chloride, 0.01% |
| | pilocarpine | 0.3% | Solution or suspension | presbyopia | Any, benzalkonium chloride, 0.01% |
| | pilocarpine | varies with severity of presbyopia, 0.3%-2.2% | Solution or suspension | presbyopia | Any, benzalkonium chloride, 0.01% |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for removing a preservative from a formulation comprising a therapeutic agent, the device comprising:
   a nozzle comprising:
   a fluid outlet;
   an inlet cap comprising one or more apertures, the one or more apertures in the inlet cap comprising a fluid inlet;
   a flow diverter, wherein the flow diverter is configured to limit a flow between the fluid inlet and the fluid outlet when the device is not in use, wherein the flow diverter is configured to divert regions of a fluid flow path in a plurality of different directions, a total distance along the fluid flow path through a matrix from the fluid inlet to the fluid outlet being longer than a distance along an axis from the fluid inlet to the fluid outlet; and
   the matrix disposed within the nozzle, wherein the matrix is configured to absorb at least 50 percent of the preservative from the formulation comprising the therapeutic agent and the preservative.

2. The device of claim 1, further comprising an outlet cap comprising one or more apertures, the one or more apertures in the outlet cap comprising the fluid outlet, wherein the outlet cap has a hydraulic permeability less than 10 Darcy.

3. The device of claim 2, wherein either of the inlet cap or the outlet cap comprises a screen or a mesh.

4. The device of claim 2, wherein either of the inlet cap or the outlet cap comprises a filter, wherein the filter comprises a pore size of about 0.2 microns.

5. The device of claim 2, wherein either of the inlet cap or the outlet cap is prewetted with the preservative.

6. The device of claim 2, wherein the hydraulic permeability of the inlet cap or the outlet cap is about 0.1 Darcy.

7. The device of claim 2, wherein a pore size of the one or more apertures in the inlet cap or the outlet cap is less than a particle size of the matrix.

8. The device of claim 7, wherein a pore size of the one or more apertures in the inlet cap or the outlet cap is about 0.2 microns.

9. The device of claim 1, wherein a first drop of the formulation from the device and a tenth drop of the formulation from the device comprise equal concentrations of the preservative to within 10%.

10. The device of claim 1, wherein a drop of the formulation from the device dispensed on a first day and a second drop dispensed on a seventh day comprise equal concentrations of the preservative to within 10% at a drop rate of at least one drop per day.

11. The device of claim 1, wherein the formulation is forced through the nozzle from the fluid inlet to the fluid outlet and wherein forcing the formulation through the nozzle removes the preservative from the formulation.

12. The device of claim 11, wherein at least 50 percent of the preservative is removed from the formulation and wherein at least 50 percent of the therapeutic agent is retained.

13. The device of claim 11, wherein the device further comprises a reservoir containing the formulation, and wherein the reservoir is configured to have an internal pressure which increases with increasing squeeze pressure exerted by a user to form a drop.

14. The device of claim 13, wherein the squeeze pressure is within a range from 0.01 Atm to 0.5 Atm.

15. The device of claim 13, wherein the internal pressure comprises a pressure within a range from 1 Atm to 5 Atm.

16. The device of claim 13, wherein the drop is formed within a time defined by a range between 0.1 seconds and 10 seconds.

17. The device of claim 13, wherein the drop comprises a volume defined by a range between 1 μL and 100 μL.

18. The device of claim 1, wherein the inlet cap has a hydraulic permeability less than 10 Darcy.

19. The device of claim 1, wherein the hydraulic permeability of the inlet cap is less than a hydraulic permeability of the matrix.

* * * * *